(12) United States Patent
Tamai et al.

(10) Patent No.: US 6,949,553 B2
(45) Date of Patent: Sep. 27, 2005

(54) ALIPHATIC COMPOUNDS, THEIR SYNTHESIS METHOD, AND UTILIZATION OF THE SAME

(75) Inventors: Tadakazu Tamai, Ibaraki (JP); Kazuyoshi Yoshikai, Ibaraki (JP); Masazumi Nishikawa, Ibaraki (JP); Kunio Ogasawara, Miyagi (JP); Itsuki Murota, Ibaraki (JP)

(73) Assignee: Maruha Corporation, Tokyo (JP)

( * ) Notice: Subject to any disclaimer, the term of this patent is extended or adjusted under 35 U.S.C. 154(b) by 0 days.

(21) Appl. No.: 10/481,062

(22) PCT Filed: Jun. 18, 2002

(86) PCT No.: PCT/JP02/06067

§ 371 (c)(1),
(2), (4) Date: Dec. 17, 2003

(87) PCT Pub. No.: WO02/102770

PCT Pub. Date: Dec. 27, 2002

(65) Prior Publication Data

US 2004/0162435 A1 Aug. 19, 2004

(30) Foreign Application Priority Data

Jun. 18, 2001 (JP) .................................. 2001-183384

(51) Int. Cl.$^7$ .................... C07D 207/09; C07D 207/14; A61K 31/40; A61K 31/495
(52) U.S. Cl. ............................. 514/252.12; 514/255.01; 514/426; 514/428; 548/557; 548/558; 548/568
(58) Field of Search .............................. 548/568, 557, 548/558, 537; 514/252.12, 255.01, 426, 428, 408

(56) References Cited

U.S. PATENT DOCUMENTS

| 3,284,177 A | 11/1966 | Lindstrom |
| 2004/0014816 A1 | 1/2004 | Tamai et al. |

FOREIGN PATENT DOCUMENTS

| GB | 1 534 111 | 11/1978 |
| JP | 50-120485 A | 9/1975 |
| JP | 52-131507 A | 11/1977 |
| JP | 57-28037 A | 2/1982 |
| JP | 60-123451 A | 7/1985 |
| WO | WO 02/30872 A1 | 4/2002 |

OTHER PUBLICATIONS

Kiuchi et al., Chemical and Pharmaceutical Bulletin, 40(12), 3234–3244, 1992.*
Wang et al., Experimental Studies of Structure and Inhibition Efficiency of Imidazoline Derivatives, Journal of Chinese Society for Corrosion and Protection, vol. 21, No, 2, pp. 116–122 (2001) (English abstract also provided).

* cited by examiner

Primary Examiner—Fiona T. Powers
(74) Attorney, Agent, or Firm—Birch, Stewart, Kolasch & Birch, LLP

(57) ABSTRACT

The present invention relates to aliphatic compounds of the formula I, or stereoisomers thereof, or their pharmaceutically acceptable salts:

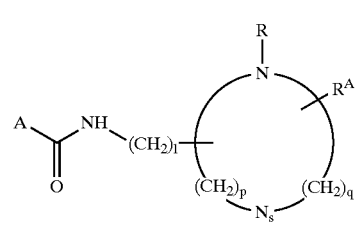

wherein A represents an optionally substituted $CH_3C_nH_{(2n-2m)}$— (wherein n denotes an integer of 4 to 22, and m represents an unsaturation number which is an integer of 0 to 7), l represents an integer of 0 to 10, s represents 0 or 1, provided that when s is 0, p+q=4 or 5, but when s is 1, p+q=3 or 4, and in each case, either p or q is an integer of 1 or more, R represents an alkyl group having 1 to 10 carbon atoms which may be straight-chain or branched-chain, and $R^A$ represents hydrogen or an alkyl group having 1 to 10 carbon atoms which may be straight-chain or branched-chain, and their use in suppression of platelet aggregation, in suppression of inflammation, and in prevention and treatment of circulatory diseases.

10 Claims, 10 Drawing Sheets

ALIPHATIC COMPOUNDS, THEIR SYNTHESIS METHOD, AND UTILIZATION OF THE SAME

TECHNICAL FIELD

This invention relates to novel aliphatic compounds, pharmaceutical compositions containing them, and their use in the suppression of platelet aggregation, the suppression of inflammation, and the prevention and treatment of circulatory diseases.

BACKGROUND ART

When platelets in the blood contact subendothelial tissue after vascular endothelial cells are injured and peeled, they adhere thereto and cause an aggregation reaction. This reaction brings about thrombus formation, causing vascular disorders including thrombosis.

In the prevention and treatment of such diseases, therefore, it is important to elucidate platelet functions and consider how platelet aggregation should be suppressed.

In connection with adhesion and aggregation functions among the platelet functions, the following theory is currently held: When a stimulant, such as collagen, arachidonic acid, ADP, thrombin, serotonin or epinephrine, stimulates corresponding receptors on the platelet membrane, the glycoprotein conjugate GPIIb-IIIa on the membrane becomes capable of binding to fibrinogen in the blood via the stimulus conducting system. As a result, platelets are mutually crosslinked and aggregated.

Much still remains unknown about the actions of the above substances working as stimulants. However, it is speculated that stimuli from various stimulants including collagen activate phospholipase A2 to produce arachidonic acid from phospholipid, and the resulting arachidonic acid is metabolized into prostaglandins $(PG)G_2$ and $PGH_2$ by cyclooxygenase (COX), and further into thromboxane (TX) $A_2$.

Also, the actions of the above stimulants are different. Stimuli from the stimulants, other than epinephrine and collagen, to platelets cause influx of Ca ions from outside of cells, and mobilize Ca ions from Ca storage granules, thereby raising intracellular Ca ion concentration. This causes the structural change of GPIIb-IIIa and contraction of contractile protein, arousing platelet aggregation and release reactions. With collagen, such reactions have not been observed.

In terms of the mechanism of exhibition of such platelet functions, antiplatelet drugs currently developed are classified into those acting on stimulus receptors, those acting on the stimulus conducting system (PG metabolism system inhibitors, those involved in cAMP metabolism), and those acting on GPIIb-IIIa.

GPIIb-IIIa receptor antagonists inhibit the terminal point of the aforementioned platelet reaction, and thus inhibit every platelet reaction, regardless of the cause of the platelet reaction. On the other hand, the potency of conventional GPIIb/IIIa receptor antagonists is such that its effective dose in single dose treatment is about 0.1 to 1 mg/kg by the intravenous route. Thus, this potency cannot be said to be sufficiently high.

Hence, antiplatelet drugs, which suppress platelet aggregation potently, are desired.

DISCLOSURE OF THE INVENTION

We, the present inventors, conducted in-depth studies in the light of the above facts. As a result, we newly discovered compounds represented by the general formula I shown below, or their stereoisomers, and have found that these compounds (hereinafter, referred to as "compounds of the present invention" including their stereoisomers) show a much more potent action of suppressing platelet aggregation than that of conventional GPIIb/IIIa receptor antagonists, and further exhibit an anti-inflammatory action. The present invention is based on this finding, and its object is to provide novel aliphatic compounds, a method for their production, and pharmaceuticals comprising them.

The present invention relates to aliphatic compounds of the general formula I, or stereoisomers thereof, or their pharmaceutically acceptable salts:

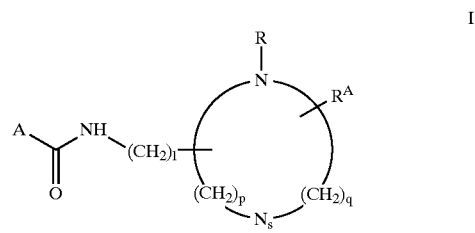

wherein

A represents an optionally substituted $CH_3C_nH_{(2n-2m)}$— where n denotes an integer of 4 to 22, and m represents an unsaturation number which is an integer of 0 to 7, l represents an integer of 0 to 10, s represents 0 or 1, provided that when s is 0, p+q=4 or 5, but when s is 1, p+q=3 or 4, and in each case, either p or q is an integer of 1 or more, R represents an alkyl group having 1 to 10 carbon atoms which may be straight-chain or branched-chain, and $R^A$ represents hydrogen or an alkyl group having 1 to 10 carbon atoms which may be straight-chain or branched-chain.

(In connection with the positions of the unsaturated bonds of $CH_3C_nH_{(2n-2m)}$— in the definition of A in the formula I, the position of "C" of the amide bond NHCO is taken as 1, and the adjacent carbons are sequentially numbered 2, 3, 4 . . . to show the positions for use in the explanation offered below.)

BEST MODE FOR CARRYING OUT THE INVENTION

Figure 1:
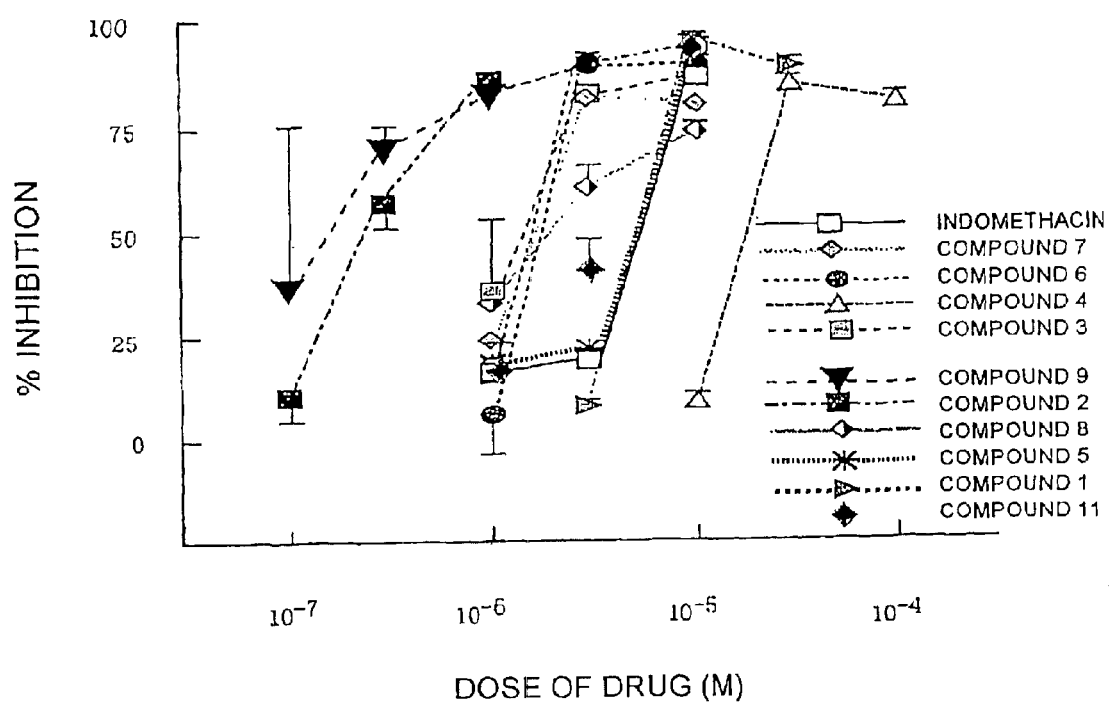
FIG. 1 is a graph showing the action, by the compounds of the present invention (Compounds 1 to 9), of suppressing platelet aggregation in vitro dose-dependently as does indomethacin.
Figure 2:
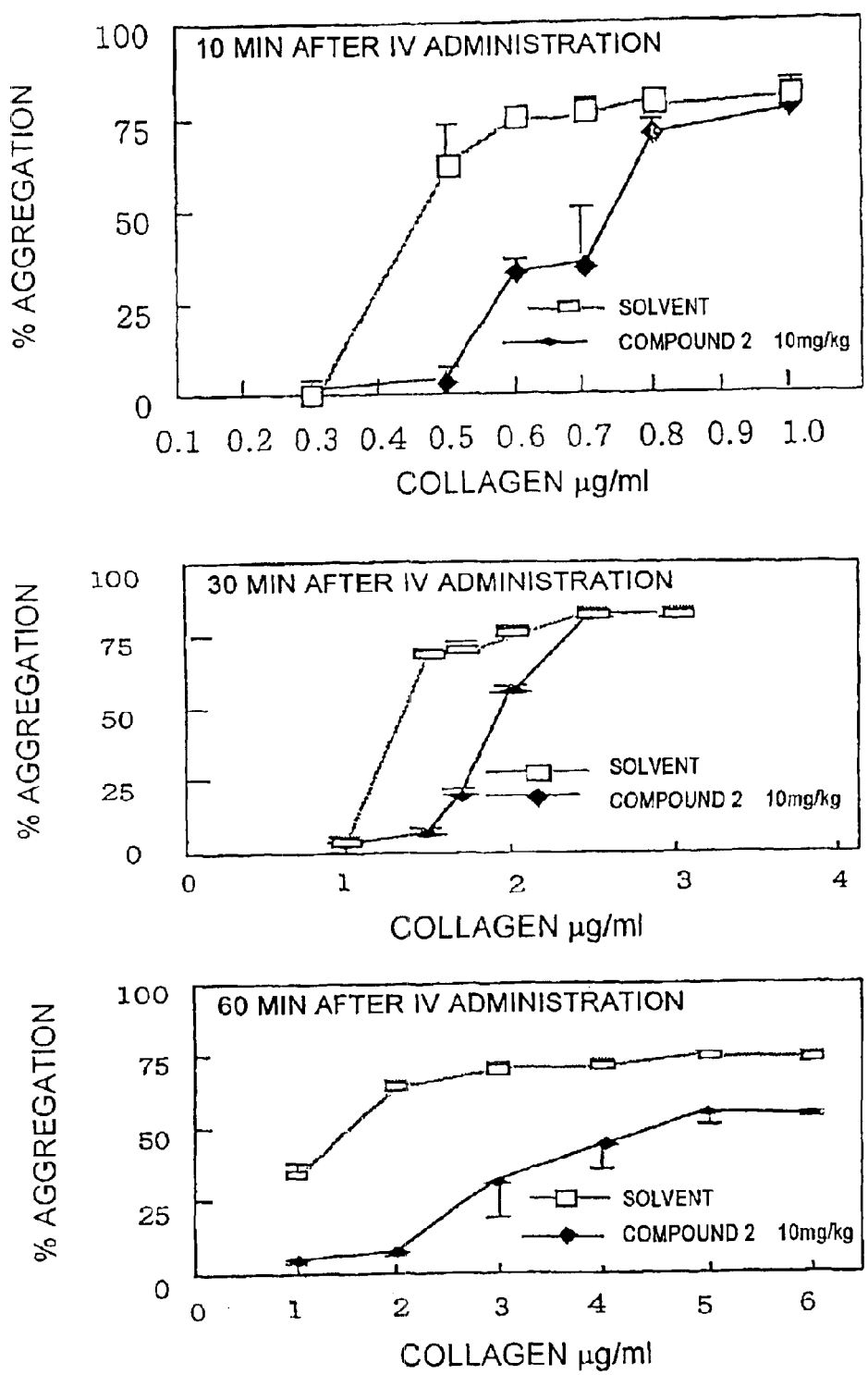
FIG. 2 is a graph showing changes over time in the action, by the compound of the present invention (Compound 2), of suppressing platelet aggregation ex vivo.

The definitions in the formula I for the compounds of the present invention will be described.

Concrete examples of the "alkyl group having 1 to 10 carbon atoms which may be straight-chain or branched-chain" are alkyl groups such as a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, an n-hexyl group, an n-heptyl group, an n-octyl group, an n-nonyl group, and an n-decyl group.

The term "optionally substituted $CH_3C_nH_{(2n-2m)}$—" refers to $CH_3C_nH_{(2n-2m)}$— may having any substituent.

Examples of the substituent include a hydroxyl group, a halogen atom, an alkyl group having 1 to 10 carbon atoms which may be straight-chain or branched-chain, a cycloalkyl group having 3 to 7 carbon atoms, and an aryl group.

Concrete examples of the "cycloalkyl group having 3 to 7 carbon atoms" include a cyclopropyl group, a cyclobutyl group, a cyclopentyl group, a cyclohexyl group, and a cycloheptyl group.

Concrete examples of the "aryl group" include a phenyl group, etc.

Concrete examples of the "alkyl group having 1 to 10 carbon atoms which may be straight-chain or branched-chain" are as described above.

Preferred embodiments of the compounds of the general formula I according to the present invention are mentioned as follows:

Preferably, p and q are such that p=q=2.

The present invention provides the compounds of the general formula I which are compounds of the following general formula II (these compounds correspond to the compounds of the general formula I wherein s=0 and p=q=2):

General Formula II

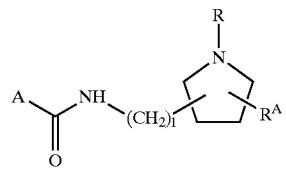

wherein R, $R^A$, A, and l have the same meanings as the meanings of the symbols in the formula I.

In the above general formula II, the preferred substitution position of A—CONH—$(CH_2)_l$— is at the carbon adjacent to N—R.

The present invention provides the compounds of the general formula I which are compounds of the following general formula III (these compounds correspond to the compounds of the general formula I where s=1 and p=q=2):

General Formula III

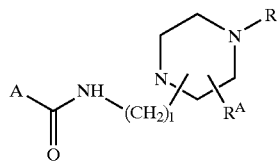

where R, $R^A$, A, and l have the same meanings as the meanings of the symbols in the formula I.

In the above general formula III, the preferred substitution position of A—CONH—$(CH_2)_l$— is at the nitrogen atom of the piperazine ring.

In the compounds of the general formulas I to III according to the present invention, the preferred embodiments are as follows:

R is preferably methyl, ethyl, propyl, isopropyl or butyl, more preferably methyl or ethyl, and most preferably a methyl group.

$R^A$ is preferably hydrogen, but when $R^A$ is an alkyl group, it preferably has 1 to 6 carbon atoms, and more preferably it has 1 to 4 carbon atoms. The position of substitution by $R^A$ in the ring is preferably a position which is not adjacent to N—R.

l is preferably an integer of 0 to 3.

n is preferably an integer of 6 to 22, and more preferably an integer of 14 to 22.

m is preferably an integer of 1 to 7, and more preferably an integer of 2 to 6.

Preferred examples of A are derived from, but not limited to, docosahexaenoic acid (n=20, m=6) or eicosapentaenoic acid (n=18, m=5).

In connection with the positions of the unsaturated bonds of $CH_3C_nH_{(2n-2m)}$— in the definition of A, they are, preferably, the positions 9, 12 and 15 if n=16, the positions 5, 8, 11, 14 and 17 if n=18, and the positions 4, 7, 10, 13, 16 and 19 if n=20.

The optional substituent of A is preferably that which does not affect the solubility of the compounds of the formula I. If the substituent is alkyl, it is preferably an alkyl group having a low molecular weight, for example, an alkyl group having 1 to 4 carbon atom, and more preferably a methyl group. The preferred substitution position is at a position which is not in proximity to the amide bond. For example, the position is the position 3 to 23, more preferably the position 3 to 20.

Preferred examples of A having the substituent, if they are derivatives having the substituent OH, include hydroxylated derivatives of docosahexaenoic acid (DHA), or hydroxylated derivatives of eicosapentaenoic acid (EPA), and more preferably hydroxylated derivatives of docosahexaenoic acid (DHA). The steric configuration of the hydroxylated derivatives may be (R)-configuration or (S)-configuration.

Examples of the hydroxylated derivatives of docosahexaenoic acid (DHA) include, but not limited to, 4-OH-DHA, 10-OH-DHA, 11-OH-DHA, 14-OH-DHA, 8-OH-DHA and 17-OH-DHA.

Examples of the hydroxylated derivatives of eicosapentaenoic acid (EPA) include 12-OH-EPA, which is not limitative. (For the above hydroxylated derivatives, see J. W. Karanian et al., *The Journal of Pharmacology and Experimental Therapeutics* (1994) 270, 1105–1109.)

As the preferred compounds of the present invention, the following compounds, their optical isomers, or their pharmaceutically acceptable salts are listed:
(4Z,7Z,10Z,13Z,16Z,19Z)-N-[2-(1-methylpyrrolidin-2-yl)ethyl]docosahexaenoamide;
(4Z,7Z,10Z,13Z,16Z,19Z)-N-(4-methylpiperazin-1-yl)docosahexaenoamide;
N-[2-(1-methylpyrrolidin-2-yl)ethyl]caprylamide;
N-[2-(1-methylpyrrolidin-2-yl)ethyl]myristamide;
9Z-N-[2-(1-methylpyrrolidin-2-yl)ethyl]oleamide;
(9Z,12Z)-N-[2-(1-methylpyrrolidin-2-yl)ethyl]linoleamide;
(9Z,12Z,15Z)-N-[2-(1-methylpyrrolidin-2-yl)ethyl]linolenamide;
(5Z,8Z,11Z,14Z,17Z)-N-[2-(1-methylpyrrolidin-2-yl)ethyl]eicosapentaenoamide;
(4Z,7Z,10Z,13Z,16Z,19Z)-N-[2-(1-methylpyrrolidin-2-yl)methyl]docosahexaenoamide; and
(4Z,7Z,10Z,13Z,16Z,19Z)-N-[3-(1-methylpyrrolidin-2-yl)propyl]docosahexaenoamide.

Further preferred compounds as the compounds of the present invention are as follows:
(4Z,7Z,10Z,13Z,16Z,19Z)-N-(4-methylpiperazin-1-yl)docosahexaenoamide of the formula IV, optical isomers thereof, or their pharmaceutically acceptable salts:

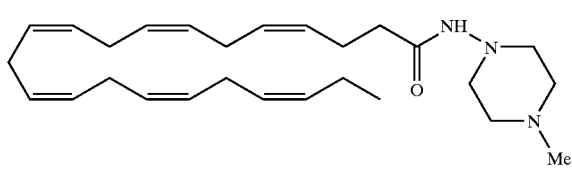

IV and (4Z,7Z,10Z,13Z,16Z,19Z)-N-[2-(1-methylpyrrolidin-2-yl)ethyl]docosahexaenoamide of the formula V, optical isomers thereof (for example, 2S-form, 2R-form) or their pharmaceutically acceptable salts:

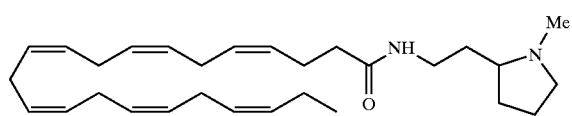

V

The stereoisomers in the present invention refer to those including any optical isomerism among (R)-forms, (S)-forms and racemic modifications, and geometric isomerism among cis-form, trans-form, and a mixture of them. As geometric isomerism, cis-form is preferred.

The pharmaceutically acceptable salts in the present invention include salts with mineral acids such as sulfuric acid, hydrochloric acid and phosphoric acid, and salts with organic acids such as acetic acid, oxalic acid, lactic acid, tartaric acid, fumaric acid, maleic acid, methanesulfonic acid, and benzenesulfonic acid. Of these salts, the salts such as hydrochloride, citrate and maleate are preferred.

The compounds of the present invention can selectively suppress platelet aggregation, especially, platelet aggregation caused by collagen. As shown by the results of experiments to be described later, the compounds of the present invention have an ex vivo platelet aggregation suppressing effect which is more potent than that of conventional GPIIb/IIIa receptor antagonists.

The compounds of the present invention can also suppress inflammation caused by inflammatory cytokines such as TNFα and PDGF.

The compounds of the present invention can be used in preventing or treating circulatory diseases.

The circulatory diseases herein refer to diseases in which the circulatory state of the blood and lymph is impaired to cause disorder to tissue or cells. These diseases include all of those which occur from various causes such as platelet aggregation and inflammatory cytokines such as TNFα and PDGF. Their examples include thrombotic diseases, arteriosclerotic diseases and hyperlipemic diseases.

The thrombotic diseases herein refer to states where the blood vessel is obstructed by thrombus, and they are classified into arterial thrombosis and venous thrombosis. Arterial thrombus occurs mainly as a complication of arteriosclerosis. Thrombus of the coronary artery becomes the cause of myocardial infarction, and thrombus of the cerebral artery becomes the cause of cerebral infarction. Venous thrombosis includes thrombosis of the superficial vein or deep vein, and deep venous thrombosis, for example, is listed.

The thrombotic diseases include, for example, unstable angina, myocardial infarction, infarction associated with a prosthetic valve, obstruction of a grafted blood vessel after a coronary artery bypass operation, transient cerebral ischemic attack, cerebral infarction, arteriosclerotic peripheral artery obstruction, erythromelalgia (thrombocythemia), thrombus of a hemodialysis shunt, angina of effort, restenosis after PTCA, and obstruction after blood vessel reconstructive operation ("Treatment of Thrombosis", published by Medical Review, 1st Ed. Jun. 20, 1996, author: Yasuo Ikeda).

The arteriosclerotic diseases herein refer to states where the arterial wall thickens and loses elasticity. Arteriosclerosis comes in three types, atherosclerosis, Mönckeberg's arteriosclerosis, and arteriolosclerosis. Examples of the arteriosclerotic diseases include cerebral infarction and cerebral hemorrhage for the cerebral artery, ischemic heart diseases such as myocardial infarction and angina pectoris for the coronary artery, aortic aneurysm and aortic dissection for the aorta, nephrosclerosis and associated renal failure for the renal artery, and obstructive arteriosclerosis for the peripheral artery.

The hyperlipemic diseases herein refer to pathologic states where serum cholesterol and/or triglyceride levels are increased. Examples are hypercholesterolemia and hyperlipidemia.

Each of the compounds in the present invention can be administered orally or parenterally (as injection, external preparation, suppository, etc.). Its dose is preferably about 0.000001 to about 100 mg/kg body weight/day, which is given as a single dose or several divided doses. More preferably, about 0.0001 to about 10 mg/kg body weight/day is given as a single dose or several doses per day. This dose may be increased or decreased depending on the type of the disease or the patient's age, body weight and symptoms.

To use the compounds of the present invention as pharmaceuticals, any forms, including a solid composition, a liquid composition and other composition, are available, and the optimal form is selected according to needs. Pharmaceutical compositions can be prepared by adding customary vehicles, bulking agents, binders, disintegration promoters, pH adjusting agents, and solubilizers to the compounds of the present invention, and forming the blends into tablets, pills, capsules, granules, powders, liquids, emulsions, suspensions, and injections by customary pharmaceutical techniques. Examples of the vehicles and bulking agents are lactose, magnesium stearate, starch, talc, gelatin, agar, pectin, gum arabic, olive oil, sesame oil, cacao butter, ethylene glycol, and other ones in customary use.

To prevent the oxidation of the preparations, it is permissible to add an antioxidant (tocopherol or the like), perform inclusion with an inclusion complexing agent such as cyclodextrin, or carry out encapsulation with a film of gelatin or the like.

Furthermore, the above compounds can be prepared, as described in Unexamined Japanese Patent Publication No. 1994-298642, in the form of O/W type emulsions with the use of phospholipids or nonionic surfactants as emulsifying agents. The emulsifying agents can be used alone or in combination of two or more, and the amount of their addition may be 0.001 to 10% (W/V), preferably 0.01 to 5% (W/V), as desired.

As the phospholipids, soybean-derived phospholipid, egg yolk-derived phospholipid, lysolecithin, phosphatidylcholine (lecithin), and phosphatidylserine can be used alone or in combination. As the nonionic surfactants, the following can be preferably used alone or in combination, but without limitation: polyoxyethylene-polyoxypropylene block copolymers having a molecular weight of 500 to 15,000 (for example, Pluronic F-68), polyalkylene glycols having a molecular weight of 1,000 to 10,000, polyoxyalkylene copolymers having a molecular weight of 1,000 to 20,000, hydrogenated castor oil polyoxyalkylene derivatives, castor oil polyoxyalkylene derivatives, glycerin esters of fatty acids, polyglycerin esters of fatty acids, sorbitan esters of fatty acids, polyoxyethylene castor oil, hydrogenated castor oil, polyoxyethylene alkyl ethers, and sucrose fatty acid esters.

The compounds of the present invention can be produced in the following manner:

These compounds can be produced by an amidation method using, as the starting materials, amines of the formula VI:

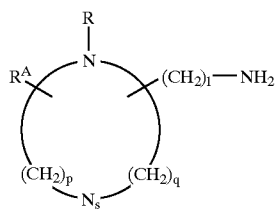

VI wherein l represents an integer of 0 to 10, s represents 0 or 1, provided that when s is 0, p+q=4 or 5, but when s is 1, p+q=3 or 4, and in either case, either p or q is an integer of 1 or more, R represents an alkyl group having 1 to 10 carbon atoms which may be straight-chain or branched-chain, and $R^A$ represents hydrogen or an alkyl group having 1 to 10 carbon atoms which may be straight-chain or branched-chain, and compounds of the formula VIII: A—$CO_2$—R' wherein R' represents hydrogen or an alkyl group having 1 to 4 carbon atoms, and A represents an optionally substituted $CH_3C_nCH_{(2n-2m)}$— wherein n denotes an integer of 4 to 22, and m represents an unsaturation number which is an integer of 0 to 7.

The amines of the formula VI, as the starting material, can be synthesized in the usual manner.

The carboxylic acids or carboxylic acid esters of the formula VIII, as the starting material, can be synthesized in the usual manner. The esters can be produced by an ordinary ester-forming reaction from the corresponding carboxylic acids or salts thereof. The corresponding carboxylic acids or salts thereof may be synthetic substances or naturally occurring substances. The synthetic substances are advantageous in terms of economy, but the naturally occurring substances are preferred because of lower toxicity. As the naturally occurring substances, those separated and purified from fish, etc., for example, can be included.

The carboxylic acids or carboxylic acid esters of the formula VIII, which have substituents, may be naturally occurring products or synthetic products.

The method of introducing the substituent during synthesis may be a method usually employed by one of ordinary skill in the art, for example, the method of introducing the substituent into the carboxylic acid or ester of the formula VIII by a substitution or addition reaction.

If the substituent is an alkyl group, the alkyl group may be introduced into $CH_3C_nH_{(2n-2m)}$COOH by use of an alkylating agent.

If the substituent is an OH group, the compounds at issue can be synthesized, without limitation, by hydroxylating naturally occurring DHA, and fractionating the hydroxylated DHA by HPLC or the like. For example, the compounds can be obtained by adding 10 to 200 mM of DHA, as a substrate, to a suspension of rainbow trout branchial cells or epithelial cells, mammalian platelets, or a human leukocyte-derived established cell line such as RBL-1, and reacting the mixture at 10 to 37° C. for 1 to 50 minutes. The reaction solution is acidified (with formic acid, acetic acid or trichloroacetic acid) to terminate the reaction. Then, the respective OH derivatives can be extracted with an organic solvent (chloroform, methanol, ethyl acetate, acetonitrile, etc.), and fractionated by a method, such as HPLC or thin layer chromatography, using a development solvent (chloroform, methanol, ethyl acetate, acetonitrile, water, or trifluoroacetic acid). However, these methods are not limitative. The respective OH derivatives can also be prepared by selective methods of synthesis using site-specific enzymes. The derivatives, such as 4-OH-DHA, 10-OH-DHA, 11-OH-DHA, 14-OH-DHA, 8-OH-DHA, and 17-OH-DHA (S-forms thereof) are commercially available from Wako Pure Chemical Industries.

In obtaining the starting materials by synthesis, the amines of the formula VI or the carboxylic acids or esters of the formula VIII may be separated, or can be used dissolved in solvents.

The amidation method is not limited, but the targeted compound can generally be synthesized by the mixed acid anhydride method. For example, the following methods can be named here:

(1) Weinreb Method

The compound of the present invention can be produced by reacting the ester of the formula VIII with the reaction product formed between the amine of the formula VI and a trialkylaluminum, especially $(CH_3)_3Al$. This reaction will be described in detail using the following scheme (for convenience's sake, the scheme shows the ester of the formula VIII as not substituted by a substituent):

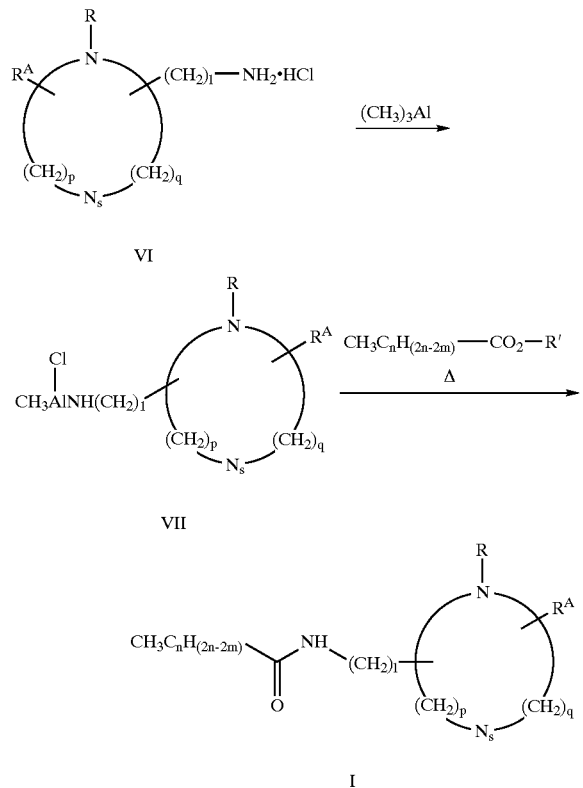

The reaction for formation of the compound VII in the above first step is performed by reacting the amine of the formula VI (preferably, an acid-addition salt such as a hydrochloride) with $(CH_3)_3Al$. This reaction is preferably carried out, with cooling, in an aromatic hydrocarbon solvent (for example, toluene, xylene or benzene).

At this time, the amount of $(CH_3)_3Al$ is preferably 0.5 to 5.0 equivalents per equivalent of the compound VI.

The above second step is performed by reacting the compound VII, obtained in the first step, with the ester of the formula VIII. This reaction is preferably carried out, with heating, in an aromatic hydrocarbon solvent (for example, toluene, xylene or benzene). The reaction temperature is preferably 40 to 70° C. The reaction temperature preferably does not exceed about 70° C., because the exceeding temperature would make the product decomposable. The reaction time is preferably 1 to 5 hours.

At this time, the amount of the ester of the formula VIII is preferably 0.5 to 5.0 equivalents per equivalent of the compound VII.

(2) Method Using $(COCl)_2$

The compound of the present invention can also be obtained by reacting the amine of the formula VI

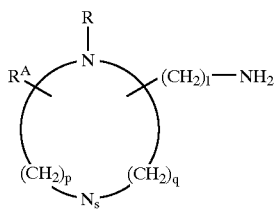

wherein p, q, s, l, R and $R^A$ are as defined above, with an acid chloride formed by the reaction between the carboxylic acid of the formula VIII: A—CO—OH [wherein A represents an optionally substituted $CH_3C_nH_{(2n-2m)}$— (wherein n denotes an integer of 4 to 22, and m represents an unsaturation number which is an integer of 0 to 7)] and $(COCl)_2$.

The above first step—the reaction for formation of the acid chloride by the reaction between the carboxylic acid of the formula VIII and $(COCl)_2$—is preferably carried out, with cooling, in an aromatic hydrocarbon solvent (for example, toluene, xylene or benzene).

At this time, the amount of $(COCl)_2$ is preferably 1 to 5 equivalents per equivalent of the carboxylic acid of the formula VIII: A—CO—OH.

The above second step—the reaction between the acid chloride obtained in the first step and the amine of the formula VI—is preferably performed in a hydrocarbon solvent (for example, dichloromethane or chloroform) or an aromatic hydrocarbon solvent (for example, toluene, xylene or benzene). The reaction temperature is preferably −5 to +5° C. The reaction temperature preferably does not exceed about +5° C., because the exceeding temperature would make the product decomposable. The reaction time is preferably 0.5 to 5 hours.

At this time, the amount of the amine of the formula VI is preferably 1 to 5 equivalents per equivalent of the acid chloride.

Whichever method of production is employed, the compound of the present invention can be isolated and purified in the usual manner (e.g. filtration, solvent extraction, recrystallization, reprecipitation or chromatography), if desired, after completion of the reaction.

The stereoisomer can be obtained by selecting suitable starting materials. In the case of a mixture of stereoisomers, stereochemically pure isomers can be obtained by chromatography or racemic resolution.

EXAMPLES

The present invention will now be described in further detail by Examples and Test Examples, which in no way limit the technical scope of the present invention.

Example 1

Synthesis of (4Z,7Z,10Z,13Z,16Z,19Z)-N-(4-methylpiperazin-1-yl)docosahexaenoamide (Compound 1)

Toluene (15 ml), dried using the molecular sieve MS 4A, was mixed with 10.3 ml of a n-hexane solution of 15% $Me_3Al$. With the mixture being cooled in an ice-methanol bath, 1.69 ml (14.1 mmols) of 1-amino-4-methylpiperazine was added dropwise over about 2 minutes (inner tempera ture <7° C.). The 1-amino-4-methylpiperazine was finally washed using 2 ml of toluene. After stirring for 35 minutes, the temperature was raised to room temperature, and 6 ml of a toluene solution of 5.0 g (14.0 mmols) of docosahexaenoic acid ethyl ester (hereinafter referred to as DHA ethyl ester) was added dropwise over 6 minutes (inner temperature 25~26° C.). After stirring for 2 hours at 70° C., the mixture was cooled with ice, and 24 ml of 0.67N hydrochloric acid was added dropwise (inner temperature raised up to 39° C.). The mixture was stirred for 10 minutes, and water and ethyl acetate were added. Then, the mixture was filtered through Celite, the filtrate was separated into respective layers, and the organic layer was washed twice with 20 ml of a saturated aqueous solution of sodium chloride. After this layer was dried over anhydrous sodium sulfate, it was concentrated under reduced pressure on a 32° C. water bath to obtain the captioned compound. This compound was subjected to silica gel column chromatography (mobile phase: CHCl₃→AcOEt→CHCl₃:MeOH (4:1)), and then further subjected to silica gel column chromatography (mobile phase: CHCl₃:MeOH (19:1)) for purification. NMR confirmed the purified compound to have the following structure (yield 5.4 g, purity 95%):

| δ (ppm) | J (Hz) | | Proton No. |
|---|---|---|---|
| 5.45–5.26 | m | 12H | 4, 5, 7, 8, 10, 11, 13, 14, 16, 17, 19, 20 |
| 2.90–2.75 | m | 14H | 6, 9, 12, 15, 18, 21, 2', 3', 5', 6' |
| 2.70–2.50 | m | 4H | 2', 3', 5', 6' |
| 2.42–2.36 | m | 2H | 3 |
| 2.33 | s | 3H | N—Me |
| 2.16 | t | 7.6 | 2H | 2 |
| 2.12–2.03 | m | | 2H | 21 |
| 0.98 | t | 7.6 | 3H | 22 |

Example 2

Synthesis of (4Z,7Z,10Z,13Z,16Z,19Z)-N-[2-(1-methylpyrrolidin-2-yl)ethyl]docosahexaenoamide (Compound 2)

Toluene (15 ml), dried using MS 4A, was mixed with 10.3 ml of a n-hexane solution of 15% Me₃Al. With the mixture being cooled in an ice-methanol bath, 2.03 ml (14.1 mmols) of 2-(2-aminoethyl)-1-methylpyrrolidine was added dropwise over about 2 minutes (inner temperature −7~+8° C.). The 2-(2-aminoethyl)-1-methylpyrrolidine was finally washed using 2 ml of toluene. After stirring for 20 minutes, the temperature was raised to room temperature, and 6 ml of a toluene solution of 5.0 g (14.0 mmols) of DHA ethyl ester was added dropwise over 2 minutes (inner temperature 28~29° C.). After stirring for 2 hours at 70° C., the mixture was cooled with ice, and 24 ml of 0.67N hydrochloric acid was added dropwise (inner temperature 12~27° C.). The mixture was stirred for 10 minutes, and water and ethyl acetate were added. Then, the mixture was filtered through Celite, the filtrate was separated into respective layers with the addition of a small amount of NaOH, and the organic layer was washed twice with 20 ml of a saturated aqueous solution of sodium chloride. After this layer was dried over anhydrous sodium sulfate, it was concentrated under reduced pressure on a 32° C. water bath to obtain the captioned compound (yield 4.7 g). This compound was subjected to silica gel column chromatography (mobile phase: CHCl₃:MeOH (19:1→9:1)) for purification. NMR confirmed the purified compound to have the following structure:

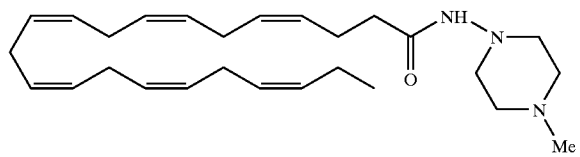

| δ (ppm) | J (Hz) | | Proton No. |
|---|---|---|---|
| 6.75 | brs | 1H | NH |
| 5.45–5.25 | m | 12H | 4, 5, 7, 8, 10, 11, 13, 14, 16, 17, 19, 20 |
| 3.46 | sextet | 6.8 | 1H | 1' |
| 3.27–3.18 | m | | 1H | 1' |
| 3.05 | ddd | 2.6, 6.8, 8.8 | 1H | 2" |
| 2.90–2.75 | m | | 10H | 6, 9, 12, 15, 18, 21 |
| 2.40 | q | 7.0 | 2H | 3 |
| 2.31 | s | | 3H | 1"(=N—Me) |
| 2.28–2.03 | m | | 6H | 2, 21, 5" |
| 1.96–1.86 | m | | 1H | 3"(or 4") |
| 1.82–1.65 | m | | 3H | 3" and/or 4" and/or 2' |
| 1.64–1.52 | m | | 2H | 3" and/or 4" and/or 2' |
| 0.98 | t | 7.6 | 3H | 22 |

Example 3

Synthesis of N-[2-(1-methylpyrrolidin-2-yl)ethyl]caprylamide (Compound 3)

Toluene (1.0 ml), dried using MS 4A, was mixed with 1.48 ml of a n-hexane solution of 15% Me₃Al. With the mixture being cooled in an ice-methanol bath, 0.25 ml (1.16 mmols) of 2-(2-aminoethyl)-1-methylpyrrolidine was added dropwise over about 2 minutes. After stirring for 20 minutes, the temperature was raised to room temperature, and 0.5 ml of a toluene solution of 0.2 g (1.16 mmols) of caprylic acid ethyl ester was added dropwise over 1 minute. After stirring for 2 hours at 70° C., the mixture was cooled with ice, and 10 ml of 1N NaOH was added dropwise. The mixture was stirred for 10 minutes, and water and ethyl acetate were added. Then, the mixture was separated into respective layers, and the organic layer was washed twice with 20 ml of a saturated aqueous solution of sodium chloride. After this layer was dried over anhydrous magnesium sulfate, it was concentrated under reduced pressure on a 30° C. water bath to obtain the captioned compound (yield 0.22 g). This compound was subjected to silica gel column chromatography (mobile phase: CHCl₃:MeOH (19:1→9:1)) for purification. NMR and mass spectrum confirmed the purified compound to have the following structure:

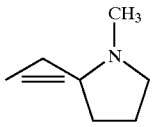

| Chemical shift | Proton No. | Assigned to: | m/z | Assigned to: |
|---|---|---|---|---|
| | | | Molecular weight: 254.41 | |
| 0.88 | 3(t, J=6.8 Hz) | H-8 | 254 (M+) | — |
| 1.29 | 8(m) | —CH₂— | 239 (M+-15) | CH₃ |
| 1.59 | 2(m) | 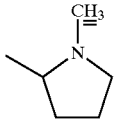 | 170 (M+-84) | C₅H₁₀N |
| 2.14 | 2(m) | H-2 | 155 (M+-99) | C₇H₁₅ |
| 2.31 | 3(sz) | 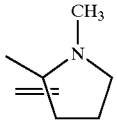 | 84 (M+-170) | C₁₀H₂₀NO |
| 3.46 | 1(q, J=6.7 Hz) | | | |
| 6.71 | 1(s) | —NH— | | |

Example 4

Synthesis of N-[2-(1-methylpyrrolidin-2-yl)ethyl] myristamide (Compound 4)

Toluene (1.00 ml), dried using MS 4A, was mixed with 1.00 ml of a n-hexane solution of 15% Me₃Al. With the mixture being cooled in an ice-methanol bath, 0.17 ml (0.78 mmol) of 2-(2-aminoethyl)-1-methylpyrrolidine was added dropwise over about 2 minutes. After stirring for 20 minutes, the temperature was raised to room temperature, and 0.5 ml of a toluene solution of 0.2 g (0.78 mmol) of myristic acid ethyl ester was added dropwise over 1 minute. After stirring for 2 hours at 70° C., the mixture was cooled with ice, and 1N NaOH solution was added dropwise. The mixture was stirred for 10 minutes, and water and ethyl acetate were added. Then, the mixture was separated into respective layers, and the organic layer was washed twice with 20 ml of a saturated aqueous solution of sodium chloride. After this layer was dried over anhydrous magnesium sulfate, it was concentrated under reduced pressure on a 30° C. water bath to obtain the captioned compound (yield 0.25 g). This compound was subjected to silica gel column chromatography (mobile phase: CHCl₃:MeOH (19:1→9:1)) for purification. NMR and mass spectrum confirmed the purified compound to have the following structure:

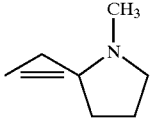

| Chemical shift | Proton No. | Assigned to: | m/z | Assigned to: |
|---|---|---|---|---|
| | | | Molecular weight: 338.566 | |
| 0.88 | 3(t, J=6.6 Hz) | H-14 | 388 (M+) | — |
| 1.27 | 20(m) | —CH₂— | 323 (M+-15) | CH₃ |
| 1.59 | 2(m) | | 170(M+-168) | C₉H₁₆N₂O |
| 2.14 | 2(m) | H-2 | 84 (M+-254) | C₁₆H₃₃NO |

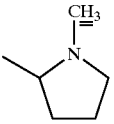

| Chemical shift | Proton No. | Assigned to: | m/z | Assigned to: |
|---|---|---|---|---|
| | | Molecular weight: 338.566 | | |
| 2.31 | 3(s) | ![CH3-pyrrolidine] | | |
| 3.46 | 1(q, J=6.6 Hz) | ![CH3-pyrrolidine] | | |

Example 5

Synthesis of 9Z-N-[2-(1-methylpyrrolidin-2-yl)ethyl]oleamide (Compound 5)

Toluene (18 ml), dried using MS 4A, was mixed with 12.3 ml of a n-hexane solution of 15% Me₃Al. With the mixture being cooled in an ice-methanol bath, 2.42 ml (16.7 mmols) of 2-(2-aminoethyl)-1-methylpyrrolidine was added dropwise over about 5 minutes. The 2-(2-aminoethyl)-1-methylpyrrolidine was finally washed using 2 ml of toluene. After stirring for 20 minutes, the temperature was raised to room temperature, and 7 ml of a toluene solution of 5.0 g (16.9 mmols) of oleic acid methyl ester was added dropwise over 2 minutes. After stirring for 2.5 hours at 70° C., the mixture was cooled with ice, and 30 ml of 0.67N hydrochloric acid was added dropwise. An aqueous solution of 1N NaOH (about 100 ml) was added, and the mixture was extracted with about 100 ml of ethyl acetate. At this time, the pH of the aqueous layer was 9 to 10. The organic layer was washed twice with 20 ml of a saturated aqueous solution of sodium chloride. After this layer was dried over anhydrous sodium sulfate, it was concentrated under reduced pressure on a 32° C. water bath to obtain the captioned compound. This compound was subjected to silica gel column chromatography (BW·80S 150 g, FUJISILYSIA, mobile phase: CHCl₃:MeOH (9:1→4:1→3:1 (V/V))) for purification. The purified compound was concentrated under reduced pressure on a 35° C. water bath to obtain 4.09 g of a pale yellow liquid (10.4 mmols, yield 62%). NMR confirmed this product to have the following structure:

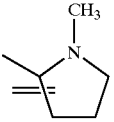

| δ (ppm) | J (Hz) | | Proton No. |
|---|---|---|---|
| 6.78 | brs | 1H | NH |
| 5.40–5.28 | m | 2H | 9, 10 |
| 3.46 | sextet | 6.8 | 1H | 1' |
| 3.28–3.18 | m | 1H | 1' |
| 3.07 | ddd | 2.8, 6.8, 8.8 | 1H | 2" |
| 2.34 | s | 3H | 1" (=Me) |
| 2.33–2.21 | m | 1H | 5" |
| 2.21–2.10 | m | 3H | 2, 5" |
| 2.03–1.97 | m | 4H | 8, 11 |
| 1.98–1.85 | m | 1H | 3" (or 4") |
| 1.80–1.70 | m | 3H | 3", 4" |
| 1.68–1.56 | m | 4H | 3, 2' |
| 1.38–1.20 | m | 20H | 4–7, 12–17 |
| 0.89 | t | 7.6 | 3H | 18 |

Example 6

Synthesis of (9Z,12Z)-N-[2-(1-methylpyrrolidin-2-yl)ethyl]linoleamide (Compound 6)

Toluene (0.7 ml), dried using MS 4A, was mixed with 0.83 ml of a n-hexane solution of 15% Me₃Al. With the mixture being cooled in an ice-methanol bath, 0.14 ml (0.98 mmol) of 2-(2-aminoethyl)-1-methylpyrrolidine was added dropwise over about 2 minutes. After stirring for 20 minutes, the temperature was raised to room temperature, and 0.4 ml of a toluene solution of 0.2 g (0.65 mmol) of linoleic acid ethyl ester was added dropwise over 1 minute. After stirring for 2 hours at 70° C., the mixture was cooled with ice, and 10 ml of a 1N NaOH solution was added dropwise (inner temperature 12~27° C.). The mixture was stirred for 10 minutes, and water and ethyl acetate were added. Then, the mixture was separated into respective layers, and the organic layer was washed twice with 20 ml of a saturated aqueous solution of sodium chloride. After this layer was dried over anhydrous magnesium sulfate, it was concentrated under reduced pressure on a 30° C. water bath to obtain the captioned compound (yield 0.114 g). This compound was subjected to silica gel column chromatography (mobile phase: $CHCl_3$:MeOH (19:1→9:1)) for purification. NMR and mass spectrum confirmed the purified compound to have the following structure:

Example 7

Synthesis of (9Z,12Z,15Z)-N-[2-(1-methylpyrrolidin-2-yl)ethyl]linolenamide (Compound 7)

Toluene (0.6 ml), dried using MS 4A, was mixed with 1.99 ml of an n-hexane solution of 15% $Me_3Al$. With the mixture being cooled in an ice-methanol bath, 0.23 ml (1.56 mmols) of 2-(2-aminoethyl)-1-methylpyrrolidine was added dropwise over about 1 minute. After stirring for 20 minutes, the temperature was raised to room temperature, and 0.2 ml of a toluene solution of 0.2 g (0.65 mmol) of linolenic acid ethyl ester was added dropwise over 1 minute. After stirring for 2 hours at 70° C., the mixture was cooled with ice, and 10 ml of a 1N NaOH solution was added dropwise. The mixture was stirred for 10 minutes, and water and ethyl acetate were added. Then, the mixture was separated into respective layers, and the organic layer was washed twice with 20 ml of a saturated aqueous solution of sodium chloride. After this layer was dried over anhydrous magne

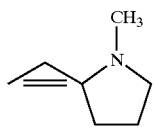

Molecular weight: 390.638

| Chemical shift | Proton No. | Assigned to: | m/z | Assigned to: |
|---|---|---|---|---|
| 0.89 | 3(t, J=6.8 Hz) | H-18 | 390 (M⁺) | — |
| 1.31 | 14(m) | —C$\underline{H}_2$— | 84(M⁺-304) | $C_{20}H_{36}NO$ |
| 1.58 | 2(m) | 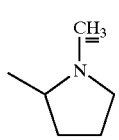 | | |
| 2.06 | 2(qn, J=7.3 Hz) | H-17 | | |
| 2.14 | 2(t, J=3.4 Hz) | H-2 | | |
| 2.31 | 3(s) | 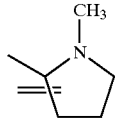 | | |
| 2.77 | 2(m) | =CHC$\underline{H}_2$CH= | | |
| 3.46 | 1(q, J=6.6 Hz) | | | |
| 5.36 | 4(m) | —C$\underline{H}$=C$\underline{H}$— | | |
| 6.70 | 1(s) | —N$\underline{H}$— | | | sium sulfate, it was concentrated under reduced pressure on a 30° C. water bath to obtain the captioned compound (yield 0.13 g). This compound was subjected to silica gel column chromatography (mobile phase: CHCl₃:MeOH (19:1→9:1)) for purification. NMR and mass spectrum confirmed the purified compound to have the following structure:

concentrated under reduced pressure on a 32° C. water bath to obtain the captioned compound. This compound was subjected to silica gel column chromatography (BW·80S 150 g, FUJISILYSIA, mobile phase: CHCl₃:MeOH (9:1→4:1→3:1 (V/V))) for purification. The purified compound was concentrated under reduced pressure on a 35° C. water bath to obtain 3.2 g (yield 57%) of a pale yellow

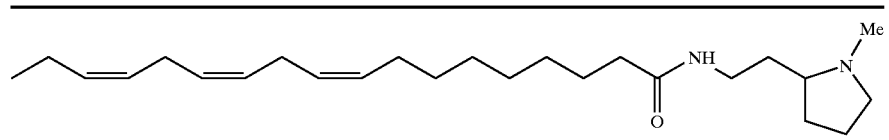

| Chemical shift | Proton No. | Assigned to: | m/z | Assigned to: |
|---|---|---|---|---|
| | | | Molecular weight: 338.622 | |
| 0.98 | 3(t, J=7.5 Hz) | H-18 | 388(M⁺) | — |
| 1.26 | 8(m) | —C$\underline{H}_2$— | 84 (M⁺-304) | C$_{20}$H$_{34}$NO |
| 1.59 | 2(m) | (CH₃–N pyrrolidine fragment) | | |
| 2.06 | 2(m) | H-17 | | |
| 2.14 | 2(m) | H-2 | | |
| 2.32 | 3(s) | (C$\underline{H}_3$–N pyrrolidine) | | |
| 2.81 | 4(m) | =CHC$\underline{H}_2$CH= | | |
| 3.46 | 1(q, J=6.6 Hz) | (CH₃–N pyrrolidine fragment) | | |
| 5.37 | 6(m) | —C$\underline{H}$=C$\underline{H}$— | | |
| 6.79 | 1(s) | —N$\underline{H}$— | | |

Example 8

Synthesis of (5Z,8Z,11Z,14Z,17Z)-N-[2-(1-methylpyrrolidin-2-yl)ethyl]eicosapentaenoamide (Compound 8)

Toluene (18 ml), dried using MS 4A, was mixed with 12.3 ml of a n-hexane solution of 15% Me₃Al. With the mixture being cooled in an ice-methanol bath, 2.42 ml (16.7 mmols) of 2-(2-aminoethyl)-1-methylpyrrolidine was added dropwise over about 5 minutes. After stirring for 20 minutes, the temperature was raised to room temperature, and 7 ml of a toluene solution of 4.5 g (13.6 mmols) of eicosapentaenoic acid ethyl ester was added dropwise over 2 minutes. After stirring for 2.5 hours at 70° C., the mixture was cooled with ice, and 30 ml of 0.67N hydrochloric acid was added dropwise. An aqueous solution of 1N NaOH (about 100 ml) was added, and the mixture was extracted with about 100 ml of ethyl acetate. At this time, the pH of the aqueous layer was 9 to 10. The organic layer was washed twice with 20 ml of a saturated aqueous solution of sodium chloride. After this layer was dried over anhydrous sodium sulfate, it was concentrated under reduced pressure on a 32° C. water bath to obtain the captioned compound. This compound was subjected to silica gel column chromatography (BW·80S 150 g, FUJISILYSIA, mobile phase: CHCl₃:MeOH (9:1→4:1→3:1 (V/V))) for purification. The purified compound was concentrated under reduced pressure on a 35° C. water bath to obtain 3.2 g (yield 57%) of a pale yellow liquid. NMR confirmed this product to have the following structure:

| δ (ppm) | J (Hz) | | Proton No. |
|---|---|---|---|
| 6.70 | brs | 1H | NH |
| 5.45–5.28 | m | 10H | 5, 6, 8, 9, 11, 12, 14, 15, 17, 18 |
| 3.47 | sextet 6.8 | 1H | 1' |
| 3.28–3.18 | m | 1H | 1' |
| 3.08 | ddd 2.8, 6.8, 8.8 | 1H | 2" |
| 2.90–2.88 | m | 8H | 7, 10, 13, 16 |
| 2.33 | s | 3H | 1" (=Me) |
| 2.33–2.20 | m | 1H | 5" |
| 2.20–2.03 | m | 7H | 2, 4, 19, 5" |
| 1.98–1.85 | m | 1H | 3" (or 4") |

-continued

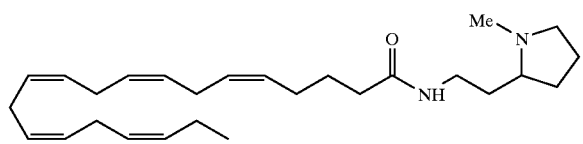

| δ (ppm) | J (Hz) | Proton No. | |
|---|---|---|---|
| 1.80–1.65 | m | 7H | 3, 2', 3", 4" |
| 0.98 | t | 7.6 | 3H | 20 |

Example 9

Synthesis of (4Z,7Z,10Z,13Z,16Z,19Z)-N-[(1-methylpyrrolidin-2-yl)methyl]docosahexaenoamide (Compound 9)

Toluene (5 ml), dried using MS 4A, was mixed with 3.2 ml of an n-hexane solution of 15% Me$_3$Al. With the mixture being cooled in an ice-methanol bath, a toluene solution (2 ml) of 0.6 g of 2-aminomethyl-1-methylpyrrolidine was added dropwise over about 2 minutes (inner temperature −10→+0° C.). After stirring for 20 minutes, the temperature was raised to 12° C., and 2 ml of a toluene solution of 1.56 g (4.38 mmols) of DHA ethyl ester was added dropwise over 2 minutes (inner temperature 10–13° C.). After stirring for 2.5 hours at 70° C., the mixture was cooled with ice, and 7.5 ml of 0.67N hydrochloric acid was added dropwise. After 35 ml of 1N NaOH was added, the mixture was extracted twice with ethyl acetate, followed by washing the extract twice with 20 ml of water and 20 ml of a saturated aqueous solution of sodium chloride. The washed product was dried over anhydrous sodium sulfate, and then concentrated under reduced pressure on a 40° C. water bath to obtain the captioned compound. This compound was subjected to silica gel column chromatography (mobile phase: CHCl$_3$:MeOH (50:1→9:1)) for purification (1.4 g, 3.3 mmols, yield 75%). NMR confirmed the purified compound to have the following structure:

| δ (ppm) | J (Hz) | | Proton No. | |
|---|---|---|---|---|
| 6.0 | brs | | 1H | NH |
| 5.45–5.25 | m | | 12H | 4, 5, 7, 8, 10, 11, 13, 14, 16, 17, 19, 20 |
| 3.61 | ddd | 2.4, 7.6, 13.6 | 1H | 1' |
| 3.20–3.00 | m | | 2H | 1', 2" |
| 2.90–2.75 | m | | 10H | 6, 9, 12, 15, 18, 21 |
| 2.45–2.33 | M | | 3H | 3, 5" |
| 2.30 | s | | 3H | 1"(=N—Me) |
| 2.28–2.17 | m | | 3H | 2, 5" |
| 2.12–2.03 | m | | 2H | 21 |
| 1.84 | dq | 11.2, 7.6 | 1H | 3" (or 4") |
| 1.75–1.62 | m | | 2H | 4" (or 3") |
| 1.60–1.51 | m | | 1H | 3" (or 4") |
| 0.98 | t | 7.6 | 3H | 22 |

Example 10

Synthesis of (4Z,7Z,10Z,13Z,16Z,19Z)-N-[2-(1-methylpyrrolidin-2-yl)ethyl]docosahexaenoamide (Compound 10)

Crude docosahexaenoic acid (DHA) (2.1 g) and 10 ml of toluene were mixed. With the mixture being cooled with ice, 0.93 ml (10.6 mmols) of (COCl)$_2$ was added, and the mixture was stirred for 2 hours at room temperature. The reaction mixture was concentrated under reduced pressure on a 40° C. water bath and, after addition of toluene, was concentrated again under reduced pressure to obtain a crude DHA acid chloride as a yellow liquid. After combining 3 ml (21 mmols) of 2-(2-aminoethyl)-1-methylpyrrolidine with 20 ml of CH$_2$Cl$_2$, the total of the crude DHA acid chloride was added under cooling with ice. The mixture was stirred for 1 hour while being cooled with ice, and 30 ml of CH$_2$Cl$_2$ and 50 ml of iced water were added. The organic layer was separated using a separating funnel, washed with 130 ml of 1M HCl, and washed twice with water. The washed layer was dried over Na$_2$SO$_4$, and subjected to silica gel column chromatography (50 g silica, mobile phase: n-hexane:ethyl acetate (9:1→3:1)) for purification, thereby obtaining 1.9 g (yield 73%) of a light yellow liquid. NMR confirmed the purified product to be the same compound as in Example 2.

Example 11

Synthesis of (4Z,7Z,10Z,13Z,16Z,19Z)-N-[3-(1-methylpyrrolidin-2-yl)propyl]docosahexaenoamide (Compound 11)

Toluene (1.34 ml), dried using MS 4A, was mixed with 0.86 ml of a n-hexane solution of 15% Me$_3$Al. With the mixture being cooled in an ice-methanol bath, 0.167 g of 2-(3-aminopropyl)-1-methylpyrrolidine in 0.6 ml of toluene was added dropwise over about 1 minute (inner temperature −15° C.). After stirring for 20 minutes, the temperature was raised to 20° C., and 0.6 ml of a toluene solution of 0.42 g (1.2 mmols) of DHA ethyl ester was added dropwise (inner temperature 20° C.). After stirring for 3 hours at 70° C., the mixture was cooled with ice, and 2.1 ml of 0.67N hydrochloric acid was added dropwise. After 10 ml of an aqueous solution of 1N NaOH was added, the mixture was extracted with ethyl acetate, followed by washing the extract with water and a saturated aqueous solution of sodium chloride. The washed product was dried over anhydrous sodium sulfate, and then concentrated under reduced pressure. The residue was purified by silica gel column chromatography (mobile phase: CHCl$_3$:MeOH (50:1→9:1→4:1)), thereby obtaining 0.21 g of the captioned compound (amount yielded: 0.46 mmol, yield: 39%, purity: 97.9%). NMR confirmed the purified compound to have the following structure:

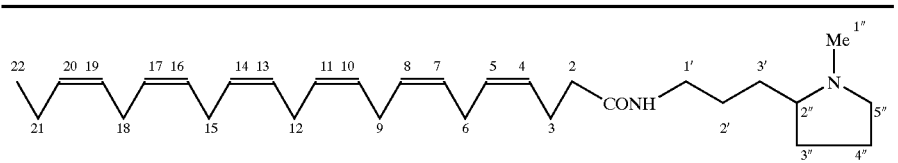

| δ (ppm) | J (Hz) | | Proton No. |
|---|---|---|---|
| 6.0 | brs | 1H | NH |
| 5.45–5.25 | m | 12H | 4, 5, 7, 8, 10, 11, 13, 14, 16, 17, 19, 20 |
| 3.37–3.28 | m | 1H | 1' |
| 3.23–3.13 | m | 1H | 1' |
| 3.08 | ddd | 2.4, 7.6, 9.2 | 1H | 2" |
| 2.90–2.75 | m | 10H | 6, 9, 12, 15, 18, 21 |
| 2.41 | q | 7.6 | 2H | 3 |
| 2.31 | s | 3H | 1" (=N—Me) |
| 2.21 | t | 7.6 | 2H | 2 |
| 2.20–2.0 | m | 2H | 5" |
| 2.12–2.03 | m | 2H | 21 |
| 1.96–1.86 | m | 1H | 3" (or 4") |
| 1.82–1.63 | m | 3H | 4" (or 3"), 2' (or 3') |
| 1.60–1.41 | m | 3H | 3" (or 4"), 2' (or 3') |
| 1.35–1.24 | m | 1H | 2' (or 3') |
| 0.98 | t | 7.6 | 3H | 22 |

Example 12

Synthesis of N-[2-((2S)-1-methylpyrrolidin-2-yl)ethyl](4Z,7Z,10Z,13Z,16Z,19Z)-docosahexaenoamide (2S-form of Compound 2)

(1) (5S)-5-[(tert-butyldimethysilyloxy)methyl]pyrrolidin-2-one

Imidazole (4.09 g, 60 mmols) and 4-dimethylaminopyridine (100 mg, 0.82 mmol) were added to a $CH_2Cl_2$ (85 ml) solution of (5S)-5-(hydroxymethyl)-2-pyrrolidinone (3.14 g, 27.3 mmols). Then, with the mixture being cooled with ice, a $CH_2Cl_2$ (15 ml) solution of tert-butyldimethylsilyl chloride (4.53 g, 30 mmols) was added, and the mixture was stirred for 15 hours at room temperature. The solvent was distilled off under reduced pressure, and then the residue was subjected to silica gel column chromatography ($SiO_2$ 300 g, MeOH—$CHCl_3$ 5:95 v/v) to obtain (5S)-5-[(tert-butyldimethylsilyloxy)methyl]pyrrolidin-2-one (6.22 g, 99.5%): $[\alpha]_D^{27}$+42.32 (c 1.136, $CHCl_3$). IR vmax (film) cm$^{-1}$: 3242, 1697. $^1$H-NMR ($CDCl_3$)δ: 5.79 (1H, br), 3.80–3.71 (1H, m), 3.63 (1H, dd, J=9.9, 3.8 Hz), 3.44 (1H, dd, J=9.9, 7.7 Hz), 2.44–2.26 (2H, m), 2.24–2.11 (1H, m), 1.80–1.67 (1H, m), 0.89 (9H, s), 0.06 (6H, s). MS m/z: 230 (M$^+$+1), 214 (M$^+$–15), 172 (100%). HRMS: Calculated for $C_{10}H_{20}NO_2Si$: 214.1263 (M$^+$–15). Found: 214.1240 (M$^+$–15).

(2) (5S)-5-[(tert-butyldimethylsilyloxy)methyl]-1-methylpyrrolidin-2-one

A THF (10 ml) solution of the (5S)-5-[(tert-butyldimethylsilyloxy)methyl]pyrrolidin-2-one (3.71 g, 16.2 mmols) was added dropwise to a THF (70 ml) suspension of NaH (60% oil disp. 778 mg, 19.4 mmols), with the system being cooled with ice, whereafter the mixture was stirred for 30 minutes at room temperature. To the mixture, MeI (5.0 ml, 81 mmols) was added during cooling with ice, and the mixture was stirred for 15 hours at room temperature. During cooling with ice, a saturated aqueous solution (50 ml) of $NH_4Cl$ was added, and the solvent was distilled off under reduced pressure. The residue was diluted with water, whereafter the dilution was extracted with AcOEt (50 ml×3), and the organic layer was dried over $MgSO_4$. The solvent was distilled off under reduced pressure, and then the residue was subjected to silica gel column chromatography ($SiO_2$ 150 g, MeOH—$CHCl_3$ 3:97 v/v) to obtain (5S)-5-[(tert-butyldimethylsilyloxy)methyl]-1-methylpyrrolidin-2-one (3.86 g, 97.9%): $[\alpha]_D^{29}$+3.46 (c 1.13, $CHCl_3$). IR vmax (film) cm$^{-1}$: 1682. $^1$H-NMR ($CDCl_3$)δ: 3.73 (1H, dd, J=10.2, 3.3 Hz), 3.60 (1H, dd, J=10.2, 4.1 Hz), 3.55 (1H, quint, J=4.1 Hz), 2.85 (3H, s), 2.50–2.37 (1H, m), 2.35–2.23 (1H, m), 2.15–2.01 (1H, m), 1.89–1.77 (1H, m), 0.89 (9H, s), 0.06 (3H, s), 0.05 (3H, s). MS m/z: 228 (M$^+$–15), 186, 98 (100%). HRMS: Calculated for $C_{11}H_{22}NO_2Si$: 228.1420 (M$^+$–15). Found: 228.1441 (M$^+$–15).

(3) (5S)-5-(bromomethyl)-1-methylpyrrolidin-2-one $Bu_4NF$ (1 mol THF solution, 17.5 ml, 17.5 mmols) was added to a THF (100 ml) solution of the (5S)-5-[(tert-butyldimethylsilyloxy)methyl]-1-methylpyrrolidin-2-one (3.84 g, 15.8 mmols), and the mixture was stirred for 15 hours at room temperature. The reaction mixture was concentrated under reduced pressure, and then the residue was subjected to silica gel column chromatography ($SiO_2$ 150 g, MeOH—$CHCl_3$ 1:9 v/v) to obtain (5S)-5-(hydroxymethyl)-1-methylpyrrolidin-2-one as a mixture (2.46 g) with inseparable impurities.

$Ph_3P$ (4.13 g, 15.75 mmols) was added to a $CH_3CN$ (35 ml) solution of the above mixture (2.46 g), and then a $CH_3CN$ (10 ml) solution of $CBr_4$ (5.22 g, 15.75 mmols) was added dropwise during cooling with ice, followed by stirring the mixture for 15 hours at room temperature. The reaction mixture was concentrated under reduced pressure, and then the residue was subjected to silica gel column chromatography ($SiO_2$ 150 g, AcOEt) to obtain (5S)-5-(bromomethyl)-1-methylpyrrolidin-2-one (2.57 g, 84.7%): IR vmax (film) cm$^{-1}$: 1688. $^1$H-NMR ($CDCl_3$)δ: 3.81 (1H, sextet, J=4.1 Hz), 3.53 (1H, d, J=4.1 Hz), 2.84 (3H, s), 2.62–2.46 (1H, m), 2.42–2.27 (1H, m), 2.26–2.14 (1H, m), 2.01–1.88 (1H, m). MS m/z: 193 (M$^+$+2), 191 (M$^+$), 98 (100%). HRMS: Calculated for $C_6H_{10}NOBr$: 190.9945 (M$^+$). Found: 190.9935 (M$^+$).

(4) 2-((2S)-1-methyl-5-oxopyrrolidin-2-yl)ethanenitrile

KCN (886 mg, 13.6 mmols), NaCN (666 mg, 13.6 mmols) and 18-crown-6 (207 mg, 1.02 mmols) were added to a $CH_3CN$ (25 ml) solution of the (5S)-5-(bromomethyl)-1-methylpyrrolidin-2-one (1.31 g, 6.8 mmols), and the mixture was heated for 43 hours under reflux. The inorganic matter was filtered off, and the filtrate was diluted with AcOEt (50 ml). The dilution was washed with a saturated solution (30 ml) of NaCl, and dried over $MgSO_4$. The solvent was distilled off under reduced pressure, and then the residue was subjected to silica gel column chromatography ($SiO_2$ 50 g, MeOH—$CHCl_3$ 1:9 v/v) to obtain 2-((2S)-1-methyl-5-oxopyrrolidin-2-yl)ethanenitrile as a mixture (1.05 g) with impurities difficult to separate: IR vmax (film) cm$^{-1}$: 2246, 1685. $^1$H-NMR ($CDCl_3$)δ: 3.85–3.76 (1H, m), 2.88 (3H, s), 2.68 (1H, dd, J=17.0, 4.4 Hz), 2.61 (1H, dd, J=17.0, 6.0 Hz), 2.62–2.48 (1H, m), 2.46–2.30 (2H, m), 2.00–1.86 (1H, m). MS m/z: 138 (M$^+$), 98 (100%). HRMS: Calcd. for $C_7H_{10}N_2O$: 138.0793 (M$^+$). Found: 138.0794 (M$^+$).

(5) 2-((2S)-1-methyl-5-thioxopyrrolidin-2-yl)ethanenitrile

Lawesson's reagent (Tokyo Kasei Kogyo) (1.54 g, 3.8 mmols) was added to a benzene (25 ml) solution of the 2-((2S)-1-methyl-5-oxopyrrolidin-2-yl)ethanenitrile (1.05 g, 7.6 mmols), and the mixture was heated for 2 hours under reflux. The solvent was distilled off under reduced pressure, and then the residue was subjected to silica gel column chromatography ($SiO_2$ 60 g, MeOH—$CHCl_3$ 1:9 v/v) to obtain 2-((2S)-1-methyl-5-thioxopyrrolidin-2-yl)ethanenitrile (941 mg, 80.6%): IR vmax (film) cm$^{-1}$: 2246. $^1$H-NMR ($CDCl_3$)δ: 4.20–4.10 (1H, m), 3.30 (3H, s), 3.25–2.98 (2H, m), 277 (1H, dd, J=17.0, 4.9 Hz), 2.68 (1H, dd, J=17.0, 6.6 Hz), 2.50–2.36 (1H, m), 2.06–1.94 (1H, m). MS m/z: 154 (M$^+$), 114 (100%). HRMS: Calcd. for $C_7H_{10}N_2S$: 154.0565 (M$^+$). Found: 154.0561 (M$^+$).

(6) N-[2-((2S)-1-methylpyrrolidin-2-yl)ethyl](4Z,7Z,10Z, 13Z,16Z,19Z)-docosahexaenoamide Raney-Ni (1.5 ml) was added to an EtOH (30 ml) solution of the 2-((2S)-1-methyl-5-thioxopyrrolidin-2-yl)ethanenitrile (940 mg, 6.1 mmols), and the mixture was heated for 24 hours under reflux (upon TCL, the starting materials had not completely disappeared). The inorganic matter was filtered off, and then the solvent was distilled off under reduced pressure. The residue was subjected to silica gel column chromatography ($SiO_2$ 40 g, MeOH—$CHCl_3$ 1:9 v/v) to obtain 2-((2S)-1-methylpyrrolidin-2-yl)ethanenitrile as a mixture (195 mg) with impurities difficult to separate.

To a THF (10 ml) suspension of $LiAlH_4$ (88 mg, 2.3 mmols), a THF (5 ml) solution of the 2-((2S)-1-methylpyrrolidin-2-yl)ethanenitrile mixture (195 mg) was added dropwise little by little, with stirring, while being cooled with ice. Then, the mixture was heated under reflux for 15 minutes. After cooling, c. $NH_4OH$ was added, and the reaction mixture was filtered using Celite. The filtrate was distilled under reduced pressure to remove the solvent, whereafter $CH_2Cl_2$ was added to the residue, and the mixture was dried over $K_2CO_3$. The solvent was distilled off under reduced pressure. $CH_2Cl_2$ (8 ml) was added to the resulting crude product, 2-((2S)-1-methylpyrrolidin-2-yl) ethylamine, then a $CH_2Cl_2$ (2 ml) solution of DHA—Cl (150 mg, 0.43 mmol) was added, and then the mixture was stirred for 15 hours at room temperature. The reaction mixture was concentrated under reduced pressure, and then the residue was subjected to silica gel column chromatography ($SiO_2$ 30 g, MeOH—$CHCl_3$ 1:9 v/v saturated with a concentrated aqueous solution of $NH_4OH$) to obtain the captioned compound (157 mg, 22.4%): $[α]_D^{24}$–6.85 (c 0.928, $CHCl_3$). $^1$H-NMR ($CDCl_3$)δ: 6.71 (1H, br), 5.45–5.26 (12H, m), 3.52–3.40 (1H, m), 3.28–3.16 (1H, m), 3.09–3.01 (1H, m), 2.90–2.77 (10H, m), 22.44–2.35 (2H, m), 2.31 (3H, s), 2.29–2.02 (6H, m), 1.97–1.82 (1H, m), 1.80–1.51 (5H, m), 0.97 (3H, t, J=7.7 Hz).

Example 13

Synthesis of N-[2-((2R)-1-methylpyrrolidin-2-yl) ethyl](4Z,7Z,10Z,13Z,16Z,19Z)-docosahexaenoamide (2R-form of Compound 2)

(1) (5R)-5-[(tert-butyldimethylsilyloxy)methyl]pyrrolidin-2-one

Imidazole (5.24 g, 77 mmols) was added to a $CH_2Cl_2$ (85 ml) solution of (5R)-5-(hydroxymethyl)-2-pyrrolidinone (4.03 g, 35 mmols). Then, during cooling with ice, a $CH_2Cl_2$ (15 ml) solution of tert-butyldimethylsilyl chloride (4.53 g, 30 mmols) was added, and the mixture was stirred for 15 hours at room temperature. The solvent was distilled off under reduced pressure, and then the residue was subjected to silica gel column chromatography ($SiO_2$ 300 g, MeOH—$CHCl_3$ 5:95 v/v) to obtain (5R)-5-[(tert-butyldimethylsilyloxy)methyl]pyrrolidin-2-one (7.92 g, 98.7%):

$[α]_D^{25}$–47.44 (c 1.80, $CHCl_3$).

(2) (5R)-5-[(tert-butyldimethylsilyloxy)methyl]-1-methylpyrrolidin-2-one

A THF (20 ml) solution of the (5R)-5-[(tert-butyldimethylsilyloxy)methyl]pyrrolidin-2-one (5.73 g, 25 mmols) was added dropwise, during cooling with ice, to a THF (100 ml) suspension of NaH (60% oil disp. 1.20 g, 30 mmols), whereafter the mixture was stirred for 30 minutes at room temperature. To the mixture, MeI (7.8 ml, 125 mmols) was added during cooling with ice, and the mixture was stirred for 15 hours at room temperature. During cooling with ice, a saturated aqueous solution (50 ml) of $NH_4Cl$ was added, and the solvent was distilled off under reduced pressure. The residue was diluted with water, whereafter the dilution was extracted with AcOEt (50 ml×3), and the organic layer was dried over $MgSO_4$. The solvent was distilled off under reduced pressure, and then the residue was subjected to silica gel column chromatography ($SiO_2$ 250 g, MeOH—$CHCl_3$ 3:97 v/v) to obtain (5R)-5-[(tert-butyldimethylsilyloxy)methyl]-1-methylpyrrolidin-2-one (6.00 g, 98.8%).

(3) (5R)-5-(bromomethyl)-1-methylpyrrolidin-2-one $Bu_4NF$ (1 mol THF solution, 14.1 ml, 14.1 mmols) was added to a THF (100 ml) solution of the (5R)-5-[(tert-butyldimethylsilyloxy)methyl]-1-methylpyrrolidin-2-one (3.43 g, 14.1 mmols), and the mixture was stirred for 15 hours at room temperature. The reaction mixture was concentrated under reduced pressure, and then the residue was subjected to silica gel column chromatography ($SiO_2$ 150 g, MeOH—$CHCl_3$ 1:9 v/v) to obtain (5R)-5-(hydroxymethyl)-1-methylpyrrolidin-2-one as a mixture (2.48 g) with inseparable impurities.

$Ph_3P$ (5.04 g, 19.2 mmols) was added to a $CH_3CN$ (60 ml) solution of the above mixture (2.48 g), and then a $CH_3CN$ (15 ml) solution of $CBr_4$ (6.37 g, 19.2 mmols) was added dropwise during cooling with ice, followed by stirring the mixture for 15 hours at room temperature. The reaction mixture was concentrated under reduced pressure, and then the residue was subjected to silica gel column chromatography ($SiO_2$ 150 g, AcOEt) to obtain (5R)-5-(bromomethyl)-1-methylpyrrolidin-2-one (2.68 g, 98.5%).

(4) 2-((2R)-1-methyl-5-oxopyrrolidin-2-yl)ethanenitrile

KCN (1.26 g, 25.7 mmols), NaCN (2.78 mg, 42.7 mmols) and 18-crown-6 (793 mg, 3 mmols) were added to a $CH_3CN$ (60 ml) solution of the (5R)-5-(bromomethyl)-1-methylpyrrolidin-2-one (2.67 g, 13.9 mmols), and the mixture was heated for 44 hours under reflux. The inorganic matter was filtered off, and the filtrate was diluted with AcOEt (50 ml). The dilution was washed with a saturated aqueous solution (30 ml) of NaCl, and dried over $MgSO_4$.

The solvent was distilled off under reduced pressure, and then the residue was subjected to silica gel column chromatography (SiO$_2$ 100 g, MeOH—CHCl$_3$ 1:9 v/v) to obtain 2-((2R)-1-methyl-5-oxopyrrolidin-2-yl)ethanenitrile as a mixture (1.49 g) with impurities difficult to separate.

(5) 2-((2R)-1-methyl-5-thioxopyrrolidin-2-yl)ethanenitrile

Lawesson's reagent (Tokyo Kasei Kogyo) (2.26 g, 5.6 mmols) was added to a benzene (40 ml) solution of the 2-((2R)-1-methyl-5-oxopyrrolidin-2-yl)ethanenitrile (1.48 g, 10.7 mmols), and the mixture was heated for 2 hours under reflux. The solvent was distilled off under reduced pressure, and then the residue was subjected to silica gel column chromatography (SiO$_2$ 80 g, MeOH—CHCl$_3$ 5:95 v/v) to obtain 2-((2R)-1-methyl-5-thioxopyrrolidin-2-yl)ethanenitrile (1.36 g, 82.8%).

(6) N-[2-((2R)-1-methylpyrrolidin-2-yl)ethyl](4Z,7Z,10Z,13Z,16Z,19Z)-docosahexaenoamide Raney-Ni (1.5 ml) was added to an EtOH (30 ml) solution of the 2-((2R)-1-methyl-5-thioxopyrrolidin-2-yl)ethanenitrile (1.36 g, 8.8 mmols), and the mixture was heated for 24 hours under reflux (Upon TCL, the starting materials had not completely disappeared). The inorganic matter was filtered off, and then the solvent was distilled off under reduced pressure. The residue was subjected to silica gel column chromatography (SiO$_2$ 40 g, MeOH—CHCl$_3$ 1:9 v/v) to obtain 2-((2R)-1-methylpyrrolidin-2-yl)ethanenitrile as a mixture (498 mg) with impurities difficult to separate.

To a THF (15 ml) suspension of LiAlH$_4$ (130 mg, 3.4 mmols), a THF (5 ml) solution of the 2-((2R)-1-methylpyrrolidin-2-yl)ethanenitrile mixture (249 mg) was added dropwise little by little, with stirring, during cooling with ice. Then, the mixture was heated under reflux for 45 minutes. After cooling, c. NH$_4$OH was added, and the reaction mixture was filtered using Celite. The filtrate was distilled under reduced pressure to remove the solvent, whereafter CH$_2$Cl$_2$ was added to the residue, and the mixture was dried over K$_2$CO$_3$. The solvent was distilled off under reduced pressure. CH$_2$Cl$_2$ (12 ml) was added to the resulting crude product, 2-((2R)-1-methylpyrrolidin-2-yl)ethylamine (257 mg), then a CH$_2$Cl$_2$ (3 ml) solution of DHA—Cl (350 mg, 1.01 mmols) was added, and the mixture was stirred for 15 hours at room temperature. The reaction mixture was concentrated under reduced pressure, and then the residue was subjected to silica gel column chromatography (SiO$_2$ 30 g, MeOH—CHCl$_3$ 1:9 v/v saturated with a concentrated aqueous solution of NH$_4$OH) to obtain the captioned compound (314 mg, 35.8%): $[\alpha]_D^{24}$+2.74 (c 0.786, CHCl$_3$).

Example 14

Production of an O/W Type Emulsion Preparation of Compound 2 (Hereinafter Referred to as Compound 2-MS)

An O/W type emulsion preparation of Compound 2 (Compound 2-MS) was produced in the following manner: Purified egg yolk lecithin (6.0 g) and 50.0 mg of Compound 2 were added to 50.0 g of purified soybean oil, and these materials were melted with heating at 40 to 45° C. To the melt, 11.5 mg of glycerin (The Pharmacopoeia of Japan) was added, and then distilled water for injection was used to give a total amount of 500 ml. The resulting mixture was formed into a coarse emulsion by means of a homomixer. The coarse emulsion was passed 5 times through a Menton-Gorin homogenizer at a pressure of 600 kg/cm$^2$, whereby it was finely emulsified. As a result, a homogenized, very fine Compound 2-MS preparation was obtained. The mean particle size and the particle size distribution of the so produced Compound 2-MS preparation were measured by Nicomp 370/Autodilute Submicron Particle Sizer (a product of Pacific Scientific). The mean particle size was 0.15 to 0.3 μm, and the particle size distribution was such that no particles measuring 1 μm or more were contained.

Test Example 1

In vitro Platelet Aggregation

Collagen-induced in vitro Platelet Aggregation

It was studied whether the compounds of the present invention would inhibit platelet aggregation induced by collagen.

Study Drugs:

The compounds of the Examples (Compounds 1 through 9 and 11) were used in experiments. These compounds were each diluted with physiological saline to end concentrations of $1\times10^{-7}$M, $3\times10^{-7}$M, $1\times10^{-6}$M, $3\times10^{-6}$M, $1\times10^{-5}$M, $3\times10^{-5}$M and $1\times10^{-4}$M.

Indomethacin was used as a positive control. Indomethacin was dissolved in methanol, and then diluted with physiological saline to end concentrations of $1\times10^{-6}$M, $3\times10^{-6}$M and $1\times10^{-5}$M.

Physiological saline was used as a negative control.

Preparation of Platelets:

After a male JW rabbit (SPF, 2.5-month old) was anesthetized, blood was withdrawn from the carotid artery into a tube containing 3.8% sodium citrate (Citral, Yamanouchi Pharmaceutical). The tube was centrifuged at 900 rpm for 10 minutes at room temperature to separate the supernatant (PRP, platelet rich plasma fraction). The residue was further centrifuged for 15 minutes at 2,500 rpm to obtain the supernatant (PPP, platelet poor plasma fraction).

Measurement of Transmittance:

PPP (platelet poor plasma fraction) was placed in a cuvette, and the cuvette was mounted in a 37° C. incubator for PPP of an aggregometer (Hematracer 240 12ch, manufactured by MCM). Then, 200 μl of PRP (platelet rich plasma fraction) was added into a cuvette, and the cuvette was mounted in a reactor for PRP. With stirring by a magnetic stirrer, the transmittance of PPP was corrected to $T_{650\ nm}$=100%, and the transmittance of PRP was corrected to $T_{650\ nm}$=0%, by automatic adjustment for 30 seconds.

The study substance (20 μl) at a predetermined concentration was added into the cuvette and, 30 seconds later, 20 μl (end concentration 0.2 μg/ml) of collagen (produced by MCM) was added. Subsequent changes in the transmittance were recorded for 5 minutes. When the platelets are aggregated, the transmittance increases. When aggregation peaked, the transmittance T at maximum aggregation was compared with the transmittance $T_0$ of the negative control, and the aggregation inhibition rate was expressed as percentage using the following equation:

Aggregation inhibition rate=$(1-T/T_0)\times 100$

From an aggregation inhibition curve obtained, a regression equation was derived by approximation of the linear type. IC$_{50}$, the point of 50% inhibition, was calculated from the regression equation.

The aggregation inhibition curve is shown in FIG. 1.

IC$_{50}$, the point of 50% inhibition of platelet aggregation, is shown in the following Table 1.

TABLE 1

50% Inhibition Point for Platelet Aggregation

| Study drug | IC$_{50}$ |
|---|---|
| Indomethacin | $(5.0 \pm 1.6) \times 10^{-6}$ M |
| Compound 1 | $(7.9 \pm 1.3) \times 10^{-6}$ M |
| Compound 2 | $(1.5 \pm 2.0) \times 10^{-6}$ M |
| Compound 3 | $(8.1 \pm 3.3) \times 10^{-6}$ M |
| Compound 4 | $(42 \pm 22) \times 10^{-6}$ M |
| Compound 5 | $(5.6 \pm 2.8) \times 10^{-6}$ M |
| Compound 6 | $(2.1 \pm 0.1) \times 10^{-6}$ M |
| Compound 7 | $(3.7 \pm 1.9) \times 10^{-6}$ M |
| Compound 8 | $(3.7 \pm 1.9) \times 10^{-6}$ M |
| Compound 9 | $(1.5 \pm 0.9) \times 10^{-6}$ M |
| Compound 11 | $(4.2 \pm 2.2) \times 10^{-6}$ M |

The above results show that Compounds 1 to 9 and 11 suppressed platelet aggregation to practically the same degree as did indomethacin.

Thus, the compounds of the present invention represented by the formula I, where n in $C_nH_{(2n-2m)}$ is an integer of 6 to 20, and the unsaturation number m in $C_nH_{(2n-2m)}$ is an integer of 0 to 6, were confirmed to have a platelet aggregation suppressing action.

In vitro Platelet Aggregation by Various Inducers

Next, the suppression of platelet aggregation by the compounds of the present invention was studied in the same manner as described above with the use of not only collagen, but also arachidonic acid, ADP, thrombin, serotonin, epinephrine and U46619 (pseudo-thromboxane A2 substance) as inducers.

As platelets, platelets prepared from rats and guinea pigs as well as rabbits were also used.

Preparation of aggregation inducers was performed in the following manner:

Collagen and ADP were purchased from MCM, and used in accordance with the method of preparation described in the manuals attached to the purchased products. Serotonin, epinephrine and thrombin were purchased from Sigma, and used as solutions in physiological saline for injection (Otsuka Pharmaceutical Factory). Arachidonic acid was purchased from Cayman, and dispersed in physiological saline for injection (Otsuka Pharmaceutical Factory) with the use of an immersion type ultrasonic oscillator (US150, NIPPON SEIKI, tip end diameter ca. 3.5 mm). U46619 (pseudo-thromboxane substance) was purchased from FUNAKOSHI, and dissolved in physiological saline for injection (Otsuka Pharmaceutical Factory) when used.

Collagen (0.1 to 1 μg/ml), arachidonic acid (1 mM), ADP (1 μM), thrombin (1 U/ml), serotonin (100 μM), epinephrine (100 to 200 μM), and U46619 (3 μM) were used.

Compound 2 was used as the study drug. Indomethacin was used as a positive control for measuring the suppression of platelet aggregation induced by collagen.

IC$_{50}$, the point of 50% inhibition of platelet aggregation, was determined, and is shown in the following Table 2.

TABLE 2

50% inhibition point, IC$_{50}$, for in vitro platelet aggregation by various inducers

| Inducer | Rabbit | Rat | Guinea pig |
|---|---|---|---|
| Collagen Compound 2 | 2.1 ± 0.8 μM | 11 ± 7 μM | 9.0 ± 6.0 μM |
| (Indomethacin) | (4.0 ± 0.5 μM) | (18 ± 7 μM) | (29 ± 23 μM) |

TABLE 2-continued

50% inhibition point, IC$_{50}$, for in vitro platelet aggregation by various inducers

| Inducer | Rabbit | Rat | Guinea pig |
|---|---|---|---|
| ADP | >100 μM | >100 μM | 65 ± 19 μM |
| Thrombin | N.A. | — | >100 μM |
| Arachidonic acid | >100 μM | N.A. | — |
| Epinephrine | — | — | N.A. |
| Serotonin | — | — | N.A. |
| U46619 | 50 ± 10 μM | N.A. | |

N.A.: No aggregation.

In the case of collagen-induced aggregation, whether the platelets from the rat or the guinea pig were used, the 50% aggregation inhibition point by Compound 2 was about $(11\pm7)\times10^{-6}$ M and $(9.0\pm6.0)\times10^{-6}$ M, respectively. These findings showed that Compound 2 exhibited a platelet aggregation inhibiting action nearly comparable to that of indomethacin, as in the case where rabbit's platelets were used.

In the case of aggregation induced by arachidonic acid, ADP and thrombin, whether the platelets from the rabbit, the rat or the guinea pig were used, it was found that Compound 2 either did not inhibit platelet aggregation, or even when it inhibited platelet aggregation, its degree of inhibition was very low.

The reason why data were not acquired in some of the experiments may have been that there were animal species differences in the activity of the platelets, and the sensitivity of the particular platelets to the particular inducers was low.

The same results as described above were obtained in the experiments using Compound 1.

Hence, the compounds of the present invention were shown to be capable of selectively suppressing platelet aggregation induced by collagen.

Human in vitro Platelet Aggregation

Preparation of Human Platelets:

From each of the large brachial veins of human volunteers, 10 ml of blood per person was drawn using an 18G syringe needle. The blood was gently dropped into a 15 ml Falcon tube containing 1 ml of 3.8% sodium citrate (Citral, Yamanouchi Pharmaceutical). A stopper for the tube was closed, and slowly inverted for mixing. Then, the blood was centrifuged at 900 rpm for 10 minutes at room temperature to separate the supernatant (platelet rich fraction, platelet rich plasma, PRP). The residue was further centrifuged for 15 minutes at 2,500 rpm to obtain the supernatant (platelet poor fraction, platelet poor plasma, PPP). The platelet density of PRP was measured with a blood cell counter (Sysmex), and diluted with PPP to adjust the platelet density to 300,000 platelets/μl.

Preparation of aggregation inducers was performed in the same manner as described earlier.

For each experiment, the doses of the inducers were so set as to obtain best evaluation of the action of the study substance. That is, the concentration of each inducer at which aggregation would clearly develop in the presence of a negative control (physiological saline) but would not excessive was set for each experiment.

If aggregation is induced by high concentration ADP or high concentration epinephrine, on the other hand, primary aggregation takes place, and then secondary aggregation proceeds again, under the action, as a trigger, of alpha granules (PDGF, serotonin, ADP, etc.) liberated from activated platelets. In the present study, the effect of the study substance on secondary aggregation due to ADP or epinephrine was also investigated.

Serotonin, when used alone, minimally causes platelet aggregation. Thus, a combination of serotonin and collagen, or a combination of serotonin and ADP was used as the inducer. The dose of the inducer was set by examining, for each experiment, the dose of each inducer which caused no aggregation when used alone, and combining doses lower than the doses which did not cause aggregation. For example, if serotonin used alone induced aggregation at a dose of 1 mM, but induced little aggregation at a dose of 0.5 mM, and if ADP alone induced aggregation at a dose of 0.25 mM, but induced no aggregation at a dose of 0.11 mM, then the doses, 0.25 mM serotonin+0.05 mM ADP, were set.

Compound 2 was used as the study substance, and the preparation of the inducers was performed in the same manner as described earlier.

The measurement of the transmittance was carried out in the same manner as described earlier.

$IC_{50}$, the point of 50% inhibition of platelet aggregation, was determined, and is shown in the following Table 3.

The results are shown in Table 2.

At any of the time points, 10 minutes, 30 minutes and 1 hour after administration of Compound 2, platelet aggregation was suppressed in comparison with the solvent group. The suppressive action was found to be such that platelet aggregation was suppressed more potently 1 hour after intravenous administration than 10 minutes or 30 minutes after administration. Thus, the time point of measurement in subsequent experiments was set to be 1 hour after administration.

The reason why platelet aggregation was suppressed more potently 1 hour after intravenous administration than 10 or 30 minutes after intravenous administration is assumed to be that this compound may gradually change into an active form in the blood, and its metabolites may contribute to its activity.

Study of Dose-dependency

It was studied whether the compound of the present invention would suppress ex vivo platelet aggregation dose-

TABLE 3

50% inhibition point, $IC_{50}$, of Compound 2 against human in vitro platelet aggregation

| Inducer | Concentration of inducer | $IC_{50}$ (M) |
|---|---|---|
| Serotonin + Collagen | (0.25~0.5) μM + (0.05~0.2) μg/ml | $(1.5 \pm 0.8) \times 10^{-5}$ |
| Serotonin + ADP | (0.25~1) μM + (0.05~0.25) μM | $(3.0 \pm 1.6) \times 10^{-6}$ |
| Collagen | (0.075~0.25) μg/ml | $(1.3 \pm 0.2) \times 10^{-5}$ |
| ADP | | |
| (primary) | (0.5~1) μM | $(3.0 \pm 1.9) \times 10^{-5}$ |
| (secondary) | (1~2.5) μM | $(5.7 \pm 2.6) \times 10^{-7}$ |
| Epinephrine | | |
| (primary) | 1 μM | $(3.3 \pm 0.6) \times 10^{-5}$ |
| (secondary) | (1~3) μM | $(2.7 \pm 1.2) \times 10^{-6}$ |
| Arachidonic acid | (1~2) μM | $(8.0 \pm 1.9) \times 10^{-5}$ |
| U46619 (pseudo-thromboxane A2) | (5~10) μM | $(5.3 \pm 2.3) \times 10^{-5}$ |
| Thrombin | (0.2~0.25) U/ml | $(5.7 \pm 0.2) \times 10^{-5}$ |

As shown in the table, whichever inducer caused aggregation, the aggregation suppressing action of Compound 2 was observed. Particularly, the suppressive action of Compound 2 against ADP-induced secondary aggregation, epinephrine-induced secondary aggregation, serotonin-induced aggregation, or collagen-induced aggregation was clearly observed. The values of the 50% suppression point, $IC_{50}$, against the respective inducers were as follows: $(5.7\pm2.6)\times10^{-7}$ M (ADP secondary aggregation), $(2.7\pm1.2)\times10^{-6}$ M (epinephrine secondary aggregation), $(3.0\pm1.6)\times10^{-6}$ M (serotonin+ADP), $(1.5\pm0.8)\times10^{-5}$ M (serotonin+collagen), and $(1.3\pm0.2)\times10^{-5}$ M (collagen).

Test Example 2

Ex vivo Platelet Aggregation
Study of the Onset of Pharmaceutical Efficacy

Compound 2 in a dose of 10 mg/kg was administered to the caudal vein of male SD rats (SPF, 8-week-old). The blood was withdrawn at three points in time, 10 minutes, 30 minutes and 1 hour after administration. Platelets were prepared from the blood samples taken, and they were used to study the aggregation rates when platelet aggregation was induced by 0.3 to 6 μg/ml of collagen. In a control group, the aggregation rates after administration of a solvent (physiological saline) were measured. The preparation of platelets and the measurement of the aggregation rates were performed in the same manner as in Test Example 1.

dependently. Compound 2 was used as the study substance, and a solvent (physiological saline) was used as a control.

Compound 2 in a dose of 1, 0.1, 0.01, 0.003, 0.001, 0.0003 or 0.0001 mg/kg was administered to the rat caudal vein. The blood was withdrawn 60 minutes after administration, and platelets were prepared from the blood. Platelet aggregation was induced by 4 to 7 μg/ml of collagen using the platelets. The preparation of platelets and the measurement of the aggregation rate were performed in the same manner as in Test Example 1.

Figure 3:
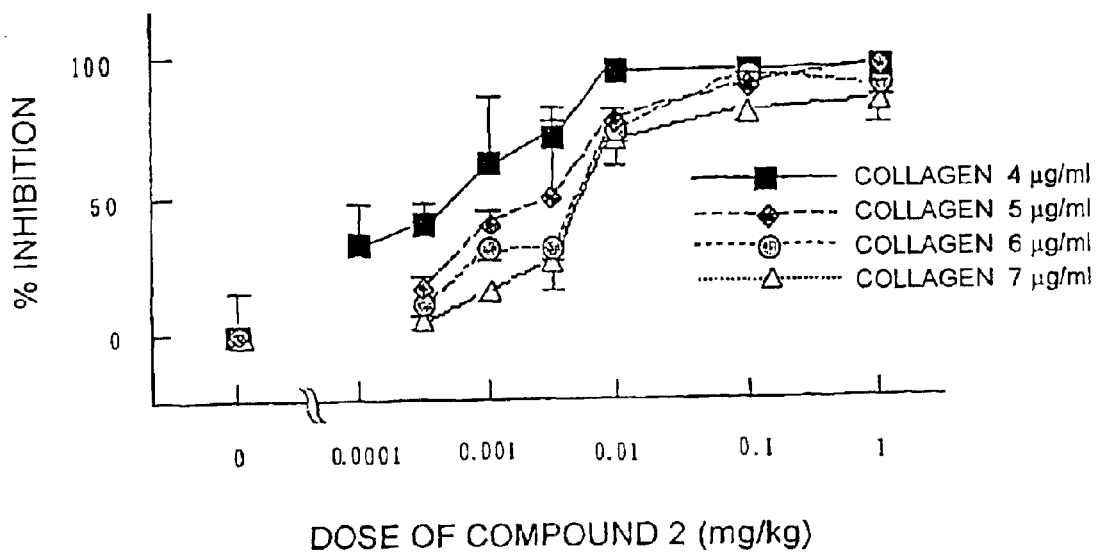
FIG. 3 is a graph showing the action, by the compound of the present invention (Compound 2), of suppressing platelet aggregation ex vivo dose-dependently.

The results are shown in FIG. 3.

In the groups receiving 1, 0.1, 0.01 or 0.001 mg/kg of Compound 2, platelet aggregation was suppressed in comparison with the solvent-treated group. In the 0.0001 mg/kg group as well, platelet aggregation induced by collagen at a low concentration of 4 μg/ml was suppressed compared with the solvent-treated group, although the suppressive action was weak.

The value of the 50% suppression point, $IC_{50}$, was 630±36 ng/kg when calculated from the data obtained when platelet aggregation was induced by 4 μg/ml of collagen. This $IC_{50}$ value for suppression of ex vivo platelet aggregation is about 1,000 times as high as that of conventional GPIIb/IIIa receptor antagonists.

Separately, Compound 5, used as the study substance, was intravenously administered in a dose of 0.1 mg/kg. The blood was withdrawn 1 hour after intravenous administration, and platelets were prepared from the blood.

Platelet aggregation was induced by 1 to 6 µg/ml of collagen using the platelets. The preparation of platelets and the measurement of the aggregation rate were performed in the same manner as in Test Example 1.

Figure 4:
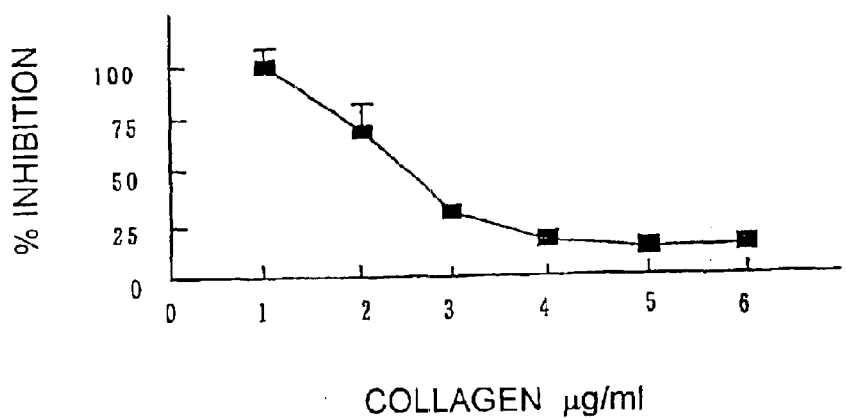
FIG. 4 is a graph showing the action, by the compound of the present invention (Compound 5), of suppressing platelet aggregation ex vivo.

The results are shown in FIG. 4.

Compound 5 was also found to suppress platelet aggregation.

(Discussion)

The action of inhibiting ex vivo platelet aggregation, shown in this Example, will be compared with the above-described action of inhibiting in vitro platelet aggregation.

The $IC_{50}$ value of 630 ng/kg, obtained in the ex vivo experiments, can be presumed to be a dose at which the blood concentration of Compound 2 reaches 26 nM, if the amount of rat blood is estimated at about 60 ml/kg. This value is smaller than the $IC_{50}$ value of 2.1±0.8 µM in the in vitro experiments, and represents a low concentration which is about 1/80 of the latter value.

That is, the action of inhibiting ex vivo platelet aggregation does not merely show that platelet aggregation is not simply suppressed by the compounds of the present invention. This action also suggests the possibility, for example, that the compounds of the present invention suppress the interaction between neutrophils and platelets involved in platelet aggregation, or that the compounds of the present invention are metabolized, and platelet aggregation is strongly suppressed in vivo while the metabolites is acting on platelets.

Test Example 3

Ex vivo Platelet Aggregation After Oral Administration

Compound 2 in a dose of 10, 1 or 0.1 mg/kg was orally administered, as a single dose, to rats with the use of a probe needle. A solvent (physiological saline) was administered as a control.

The blood was withdrawn 2 hours after administration, and platelets were prepared from the blood. Platelet aggregation was induced by 2 to 4 µg/ml of collagen using the platelets. The preparation of platelets and the measurement of the aggregation rate were performed in the same manner as in Test Example 1.

Figure 5:
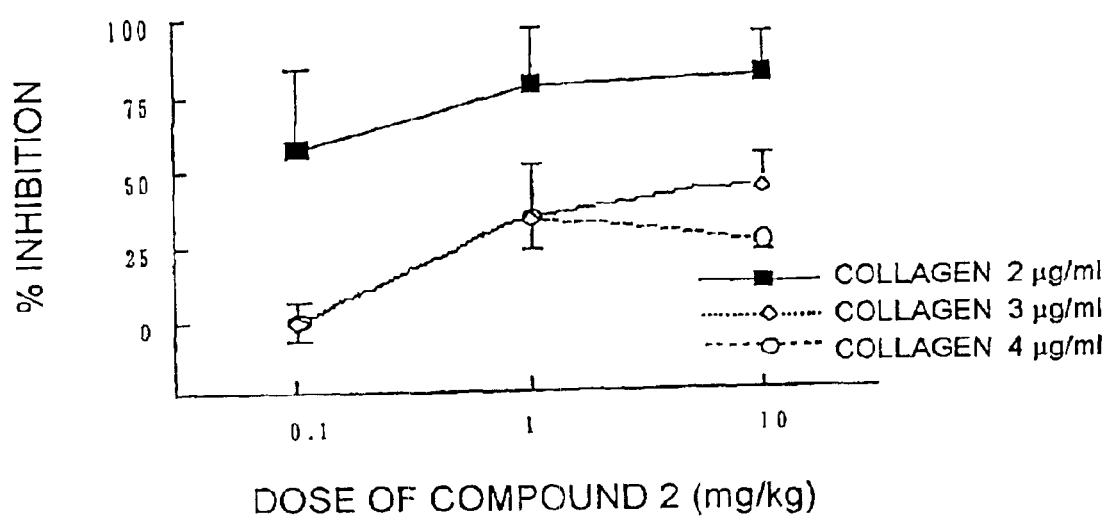
FIG. 5 is a graph showing the action, by the compound of the present invention (Compound 2) absorbed orally, of suppressing platelet aggregation.

The results are shown in FIG. 5.

Platelet aggregation was potently suppressed in the groups receiving Compound 2, as compared with the solvent-treated group.

That is, the compounds of the present invention were shown to be capable of suppressing platelet aggregation even when absorbed orally.

Test Example 4

Collagen-induced Mouse Sudden Death Model

As a preliminary study of the effect of the compounds of the present invention on an in vivo pathophysiological model, it was investigated whether the compound of the present invention would suppress collagen-induced mouse sudden death. In this model, pulmonary capillaries are obstructed by a large amount of collagen, and a sudden death is caused by oxygen deficiency. It was observed whether the compound of the present invention would suppress platelet aggregation in the body of the animal, thereby inhibiting a sudden death.

One hour after a solvent (physiological saline) or 30 µg/kg of Compound 2 was intravenously administered to mice, 37.5 mg/kg of collagen was administered to the caudal vein. One hour later, the survival rate was compared between the groups. The following results were obtained:

Survival rate in the solvent group: 2/10 mice

Survival rate in the Compound 2 group: 7/10 mice

Compound 2 showed a higher survival rate than in the solvent group.

Test Example 5

Rat Lauric Acid-induced Peripheral Circulatory Disorder Model (1) Administration After Induction of Leg Necrosis A rat lauric acid-induced peripheral circulatory disorder model, which is widely used as a peripheral circulatory disorder model, was used to investigate the effect of the compounds of the present invention on an in vivo pathophysiological model of circulatory disorder.

Lauric acid (1.5 mg/animal) was administered into the rat femoral artery to induce leg necrosis. Six hours after lauric acid administration, Compound 2 was intravenously administered as initial treatment, and then repeatedly administered once daily for 14 days.

The single dose of Compound 2 was set at 10 µg/kg, 30 µg/kg or 100 µg/kg to investigate whether this compound would ameliorate leg necrosis dose-dependently. A solvent (physiological saline) was administered as a control.

The progress of foot/leg lesions was observed 3, 7, 10 and 14 days after lauric acid administration, and evaluated by the following leg necrosis score. The score was given to each of the digits, and the sum of the scores of the respective digits was taken as a lesion index. If the disorder extended to the plantar portion, 5 points were further added.

Score 0: No lesion.
Score 1: Blackening is limited to the tiptoe.
Score 2: Blackening extends to the digital portion.
Score 3: Necrosis of the digit.
Score 4: Loss of the digit.

Figure 6:
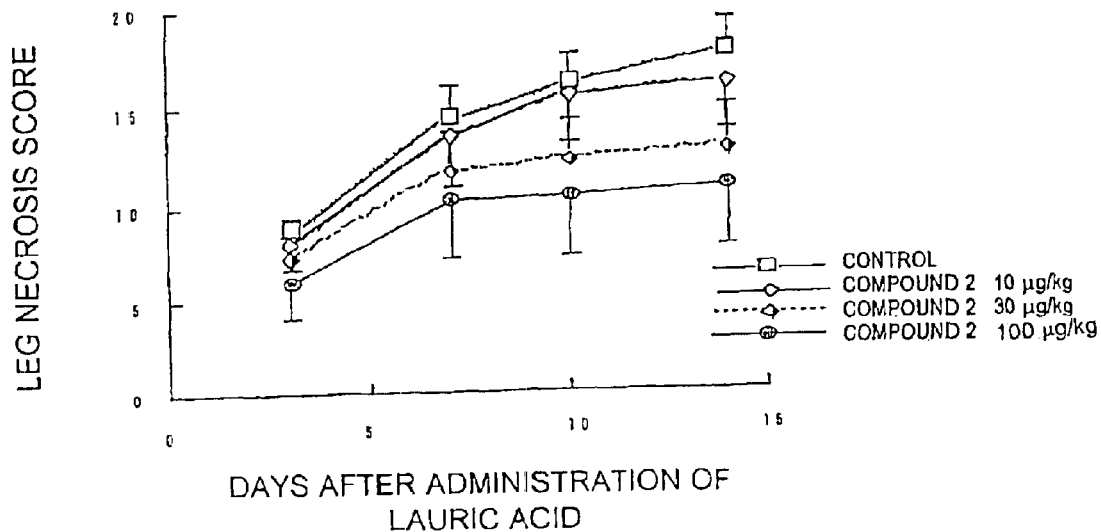
FIG. 6 is a graph showing that in the case of administration of the compound of the present invention after leg necrosis induction, the necrosis score is improved dose-dependently in a peripheral circulatory disorder model.

The results are shown in FIG. 6. Compound 2 was shown to improve the leg necrosis score dose-dependently.

(2) Administration Prior to Induction of Leg Necrosis

A test was conducted in the same manner as in (1) above, except that the administration of Compound 2 was started 1 hour before treatment with lauric acid, then Compound 2 was administered 6 hours after administration of lauric acid, and Compound 2 was further administered repeatedly once daily for 14 days. A solvent (physiological saline) was similarly administered as a control.

The progress of foot/leg lesions was observed 3, 7, 10 and 14 days after lauric acid administration, and evaluated by the above leg necrosis score.

Figure 7:
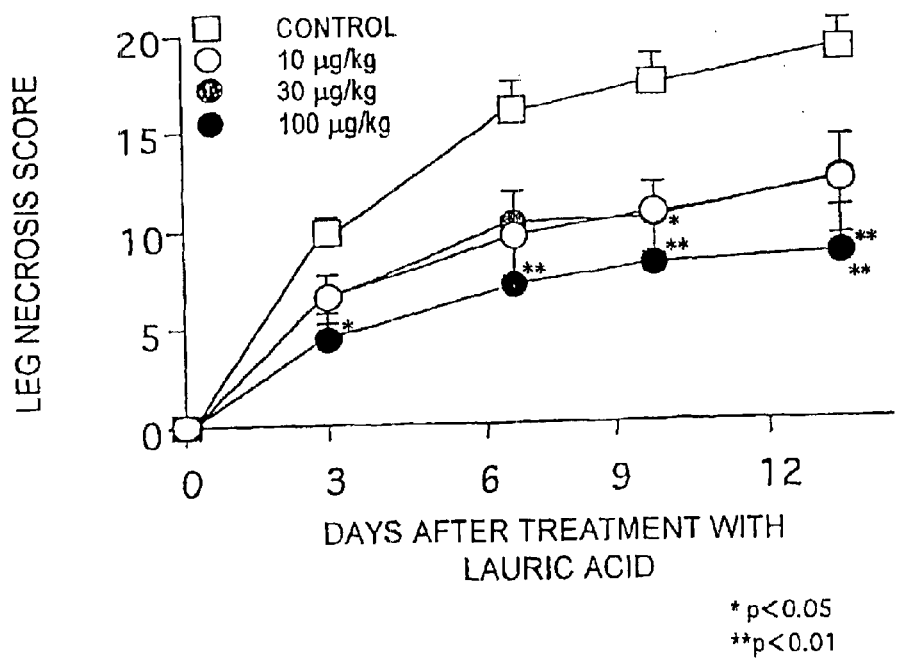
FIG. 7 is a graph showing that in the case of administration of the compound of the present invention before leg necrosis induction, the necrosis score is improved dose-dependently in a peripheral circulatory disorder model.

The results are shown in FIG. 7. Compound 2 was demonstrated to improve the leg necrosis score dose-dependently.

Upon prior administration, Compound 2 alleviated the disorder significantly in doses of 30 and 100 µg/kg, and tended to alleviate the disorder even in a dose of 10 µg/kg.

(3) Administration Prior to Induction of Leg Necrosis—O/W Emulsion Preparation

A test was conducted in the same manner as in (2) above. However, Compound 2-MS (single dose: 100 µg/kg as the amount of the active ingredient) prepared in Example 14 was used as the study drug, Palux (registered trademark) (Lipo PGE1, Taisho Pharmaceutical: single dose is 5 µg/kg as the amount of the active ingredient) or Novastan (registered trademark) (Argatroban, Mitsubishi-Tokyo Pharmaceuticals: single dose is 1 mg/kg as the amount of the active ingredient) was used as a positive control, and a solvent (physiological saline) was used as a negative control.

The progress of foot/leg lesions was observed 3, 7, 10 and 14 days after lauric acid administration, and evaluated by the above leg necrosis score.

Figure 8:
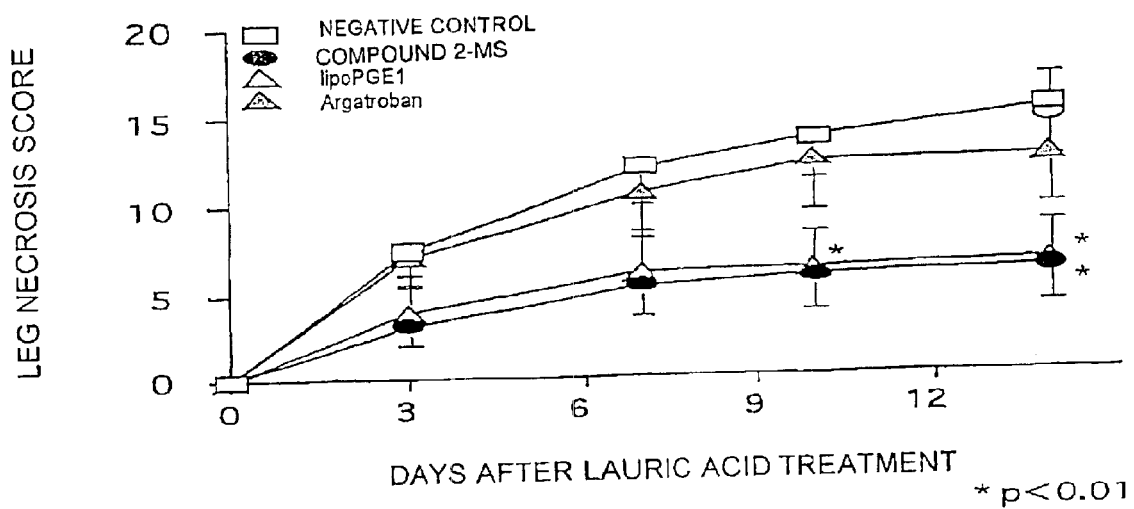
FIG. 8 is a graph showing that when an O/W emulsion of the compound of the present invention is administered before leg necrosis induction, the necrosis score is improved dose-dependently in a peripheral circulatory disorder model.

The results are shown in FIG. 8. Compound 2-MS was shown to be more potent than Argatroban and improve the leg necrosis score to a degree comparable to that of Lipo PGE1.

Test Example 6

Pseudo-blood Vessel in vitro Inflammation Model

A report says that when the inflammatory cytokine TNFα induces adhesion molecules of vascular endothelial cells and causes inflammation, whereupon neutrophils migrate to the site of inflammation, aggravating inflammation. Severe inflammation destroys the homeostasis of circulatory organs, progressing arteriosclerosis. Thus, a study was conducted on whether the compounds of the present invention have an anti-inflammatory action in a pseudo-blood vessel in vitro inflammation model using TNFα as an inflammation inducer.

Establishment of Pseudo-blood Vessel in vitro Inflammation Model

The pseudo-blood vessel in vitro inflammation model was prepared in accordance with the method described in "A Lecture on Biopharmaceutical Experiments, 12 Inflammation and Allergy II, pp. 327–341" (edited by: Kazuo Ouchi, Hirokawa Publishing Company, published May 15, 1993).

Transwells (KURABO INDUSTRIES), each separated into an upper chamber and a lower chamber by a porous polycarbonate membrane having 3 μm pores, was used. A layer of bovine endothelial cells was adhered to the bottom surface of the membrane, and cultured for 80 minutes at 37° C. in 5% $CO_2$. Then, a suspension of fluorescence-labeled neutrophils was added to the upper chamber of the transwell. Simultaneously, TNFα was suspended in the cell suspension in the upper chamber to an end concentration of 50, 25 or 17 ng/ml.

That is, in the above model, the phenomena that neutrophils pass from the upper chamber through the vascular endothelial cell layer into the lower chamber, and neutrophils adhere to the endothelial cell layer mimic a state where in response to TNFα within the blood vessel, neutrophils migrate from within the blood vessel to the site of inflammation.

The study showed that the number of neutrophils passing from the upper chamber through the vascular endothelial cell layer into the lower chamber, and the number of neutrophils adhering to the endothelial cell layer increased in a manner dependent on the concentration of TNFα. That is, TNFα was demonstrated to cause inflammation.

Effect of the Compounds of the Present Invention on the Interaction Between Neutrophils and Vascular Endothelial Cells Next, a study of how Compound 1 or Compound 2 would affect the interaction between neutrophils and vascular endothelial cells was conducted using the above pseudo-blood vessel in vitro inflammation model.

Compound 1 or Compound 2 was placed in the upper chamber of the transwells to an end concentration of 30, 3 or 0.3 μM, together with a suspension of neutrophils and 50 ng/ml of TNFα. In the same manner as described above, the number of neutrophils passing from the upper chamber through the vascular endothelial cell layer into the lower chamber, and the number of neutrophils adhering to the endothelial cell layer were measured. Based on these numbers, the neutrophil migration rate (%) was calculated. The neutrophil migration rate was expressed as the relative value (%) of the number of the migrating neutrophils in the drug treatment group with respect to the number of the migrating neutrophils in the negative control group (physiological saline).

Figure 9:
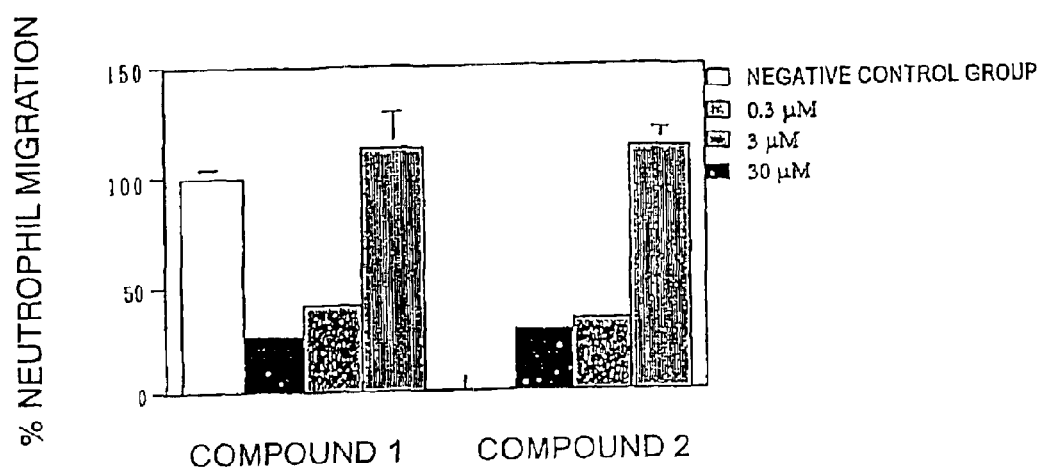
FIG. 9 is a graph showing that the compounds of the present invention (Compounds 1 and 2) act to suppress the migration of neutrophils into vascular endothelial cells.

The results are shown in FIG. 9.

Compound 1 and Compound 2 each suppressed neutrophil passage dose-dependently.

That is, the possibility was suggested that both of Compound 1 and Compound 2 work suppressively toward the interaction between neutrophils and vascular endothelial cells, and act in the direction of anti-inflammation.

Since Compound 1 or 2 acts in an anti-inflammatory manner, Compound 1 or 2 is expected to maintain homeostasis of circulatory organs and act in the direction of amelioration of pathological states.

Test Example 7

Photosensitization-induced Rat Middle Cerebral Artery Obstruction Model

A photosensitization-induced rat middle cerebral artery obstruction model, widely used as a cerebral infarction acute phase/chronic phase model, was used to investigate the effect of the compounds of the present invention on an in vivo circulatory disorder pathophysiological model.

After rats were intravenously injected with a rose bengal dye (20 mg/kg), the middle cerebral artery was irradiated with green laser light (wavelength 540 nm) for 10 minutes to induce arterial infarction due to active oxygen species. After completion of irradiation with laser light, Compound 2 was intravenously administered.

The dose of Compound 2 was set at 1 mg/kg, and whether this compound would ameliorate cerebral infarction was investigated. A solvent (physiological saline) was intravenously administered as a control.

The progress of cerebral infarction was observed 24 hours after laser light irradiation. A transverse section (1 mm in thickness) of the brain exenterated was prepared, and soaked in triphenyltetrazolium to stain living tissue red. An infarct was white, and was clearly distinguished from the living tissue. Thus, the area of the infarct was measured, and the infarct rate (the proportion of the area of the infarct to the transverse section of the brain) was calculated for use in evaluation.

Figure 10:
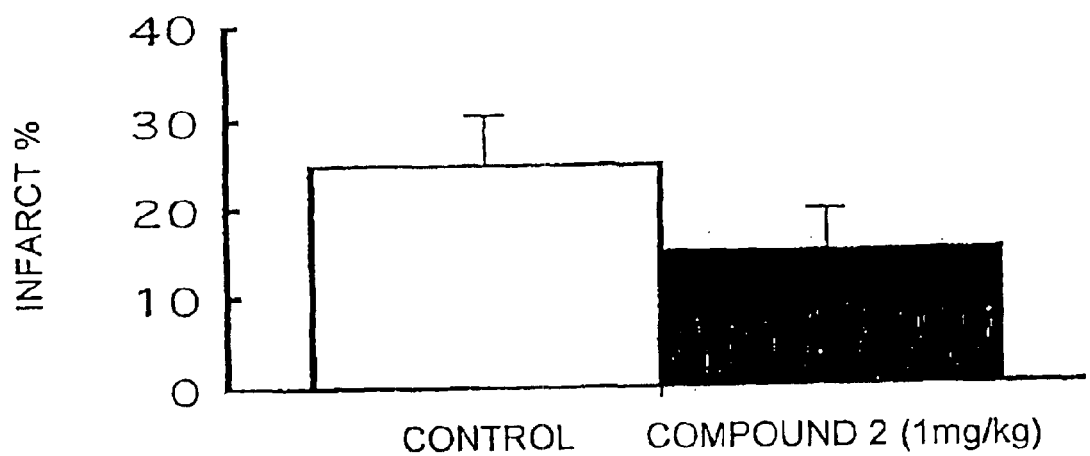
FIG. 10 is a graph showing that the compound of the present invention (Compound 2) ameliorates cerebral infarction in a middle cerebral artery obstruction model.

The results are shown in FIG. 10. Compound 2 was shown to ameliorate cerebral infarction.

Test Example 8

Rat Carotid Artery Tunica Intima Thickening Model

A rat carotid artery tunica intima thickening model, widely used as a post-PTCA restenosis model, was used to investigate the effect of the compounds of the present invention on an in vivo circulatory disorder pathophysiological model.

The tip of a balloon catheter (Fogarty catheter 2Fr, Baxter) was inserted through the rat femoral artery, and led to the carotid artery. Air (0.3 ml) was injected into the balloon to inflate the balloon. With the balloon in an inflated state, the balloon catheter was pulled out up to the aortic arch. In this manner, the carotid artery tunica intima was injured 3 times. The O/W type emulsion preparation of Compound 2 (Compound 2-MS) prepared in Example 14 was repeatedly administered intravenously once daily, beginning 1 week before vascular tunica intima injury, and repeatedly administered intravenously once daily for 2 weeks even after vascular tunica intima injury.

The single dose of Compound 2-MS was set at 100 μg/kg or 300 μg/kg (as the amount of the active ingredient) to investigate whether this compound would suppress vascular tunica intima thickening dose-dependently. An O/W type emulsion preparation, which does not contain Compound 2, was administered as a negative control. Enalapril (Sigma) was used as a positive control, and administered in a dose of 30 mg/kg once daily by the oral route in the same manner as described above.

Vascular tunica intima thickening was evaluated 2 weeks after injury. A transverse section of the carotid artery exenterated was stained with Hematoxylin-Eosin (HE), and the area of the blood vessel lumen, the area surrounded with the internal elastic lamina, and the area surrounded with the external elastic lamina were measured. Tunica intima thickening was evaluated by using the ratio of the area of the neogenetic tunica intima (the area surrounded by the internal elastic lamina –(minus) the area of the blood vessel lumen) to the area of the tunica media (the area surrounded with the external elastic lamina –(minus) the area surrounded by the internal elastic lamina).

Figure 11:
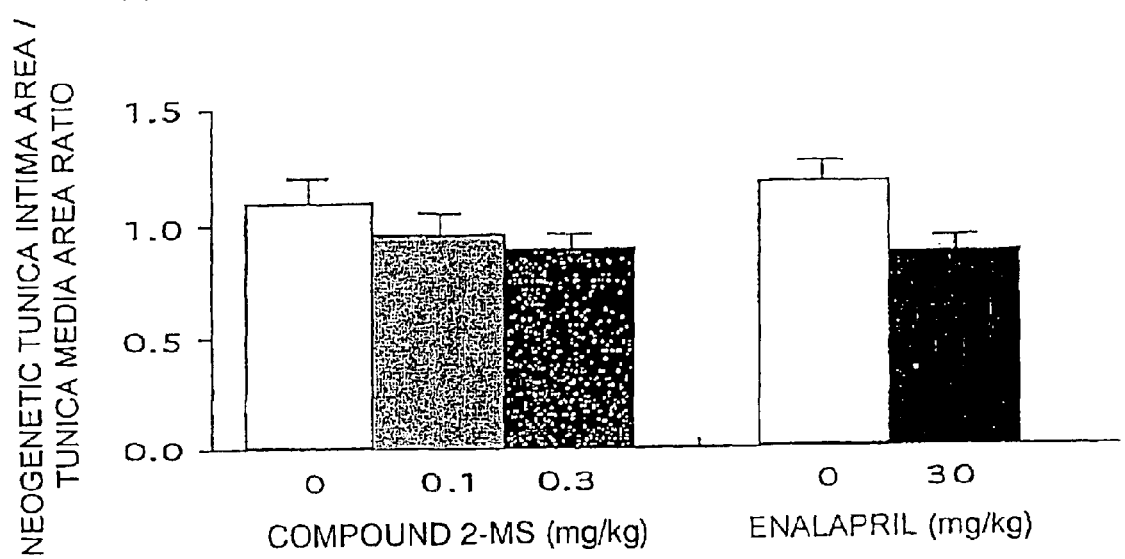
FIG. 11 is a graph showing that an O/W emulsion of the compound of the present invention suppresses vascular tunica intima thickening dose-dependently in a post-PTCA restenosis model.

The results are shown in FIG. 11. Compound 2-MS was clearly shown to suppress tunica intima thickening dose-dependently. The potency of action by 300 μg/kg of Compound 2-MS was nearly comparable to that of 30 mg/kg of enalapril.

Test Example 9

Study of Synthetic Type Vascular Smooth Muscle Cell Proliferation

The effect of the study substance on vascular smooth muscle cell proliferation was studied.

It is speculated that with the progress of arteriosclerosis, vascular smooth muscle cells are transformed from the contractile type into the synthetic type, and while secreting inflammatory cytokines such as PDGF, vascular smooth muscle cells are proliferated, resulting in the progression of arteriosclerotic lesions (Roth's hypothesis).

Thus, the effect of Compound 2 on the cell proliferation of vascular smooth muscle cells was measured in the following manner:

The rat carotid arterial tunica intima was rubbed by ballooning, and vascular smooth muscle cells were prepared by explant culture. Two weeks later, these cells were cultured in a DMEM culture medium (Gibco) containing 10% fetal bovine serum. The cultures were subcultured several times for stabilization, and then planted at a cell density of $5 \times 10^3$ cells/cm$^2$ for use in experiments. Compound 2 in combination with 50 ng/ml of the growth factor PDGF (Sigma) was added to the above planted cells and, 24 hours later, the cell density was measured by BrdU assay (Science '82, 218, p. 474, Cytometry '85, 6, p. 584). The cell density in the absence of the drug was measured as a control.

Figure 12:
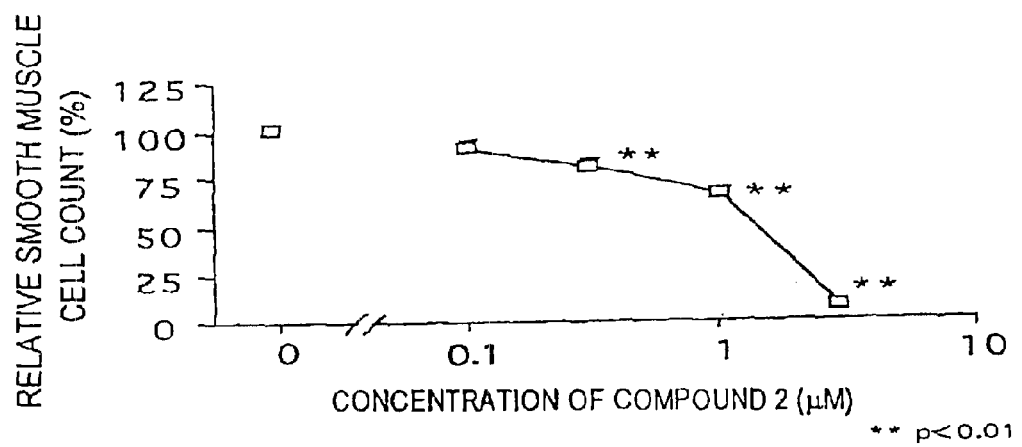
FIG. 12 is a graph showing the action, by the compound of the present invention (Compound 2), of suppressing vascular smooth muscle cell proliferation dose-dependently.

Compound 2 was found to suppress vascular smooth muscle cell proliferation concentration-dependently at a concentration of 0.3 to 3 μM. The results are shown in FIG. 12.

Relative smooth muscle cell count (%)=[cell count in the experimental group]/[cell count in the control]×100.

Industrial Applicability

The compounds of the present invention can potently suppress platelet aggregation (especially, platelet aggregation induced by collagen), can suppress inflammation, and show an excellent prophylactic or therapeutic effect on circulatory diseases (for example, thrombotic diseases, arteriosclerotic diseases or hyperlipemic diseases).

What is claimed is:

1. An aliphatic compound of the formula II, or a stereoisomer thereof, or a pharmaceutically acceptable salt of said aliphatic compound or said stereoisomer:

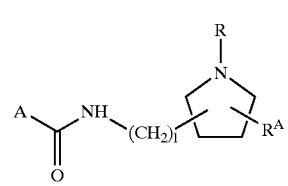

II wherein

A represents $CH_3C_nH_{(2n-2m)}$— wherein n denotes an integer of 4 to 22, and m represents an unsaturation number which is an integer of 0 to 7, l represents an integer of 0 to 10, R represents an alkyl group having 1 to 10 carbon atoms which may be straight-chain or branched-chain, and $R^A$ represents hydrogen or an alkyl group having 1 to 10 carbon atoms which may be straight-chain or branched-chain.

2. The aliphatic compound, or the stereoisomer thereof, or the pharmaceutically acceptable salt of said aliphatic compound or said stereoisomer, according to claim 1, wherein said aliphatic compound is (4Z,7Z,10Z,13Z,16Z,19Z)-N-[2-(1-methylpyrrolidin-2-yl)ethyl]docosahexaenoamide.

3. A method for producing the compound of claim 1, comprising:

reacting a compound of the formula VI'

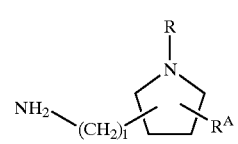

VI' wherein l, R and $R^A$ are as defined in claim 1, with a reaction product formed by a reaction between a compound of the formula A—CO—OH, wherein A represents $CH_3C_nH_{(2n-2m)}$— (wherein n and m are as defined in claim 1, and (COCl)$_2$.

4. A pharmaceutical composition comprising:

the compound or the pharmaceutically acceptable salt thereof according to claim 1 as the active ingredient; and a pharmaceutically acceptable carrier.

5. A pharmaceutical composition comprising:

the compound or the pharmaceutically acceptable salt thereof according to claim 2 as the active ingredient; and a pharmaceutically acceptable carrier.

6. A pharmaceutical composition comprising, as an active ingredient, an aliphatic compound of the formula III, or a stereoisomer thereof, or a pharmaceutically acceptable salt of said aliphatic compound or said stereoisomer:

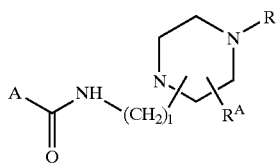

wherein

A represents an optionally substituted $CH_3C_nH_{(2n-2m)}-$ wherein n denotes an integer of 4 to 22, and m represents an unsaturation number which is an integer of 1 to 7, l represents an integer of 0 to 10, R represents an alkyl group having 1 to 10 carbon atoms which may be straight-chain or branched-chain, and $R^A$ represents hydrogen or an alkyl group having 1 to 10 carbon atoms which may be straight-chain or branched-chain; and a pharmaceutically acceptable carrier.

7. The pharmaceutical composition according to claim 6, wherein said active ingredient is (4Z,7Z,10Z,13Z,16Z,19Z)-N-(4-methylpiperazin-1-yl)docosahexaenoamide, or an optical isomer thereof, or a pharmaceutically acceptable salt of said docosahexaenoamide or said optical isomer.

8. A method of treating circulatory disease, treating or suppressing platelet aggregation, circulatory disease, obstructive arteriosclerosis, cerebral infarction, inflammation or restenosis after PTCA platelet aggregation in a patient in need thereof, said method comprising:

administering an effective amount of the compound of the formula II, or the stereoisomer thereof, or the pharmaceutically acceptable salt of the aliphatic compound or stereoisomer as defined in claim 1 or 2, to said patient.

9. A method of treating circulatory disease, treating or suppressing platelet aggregation, circulatory disease, obstructive arteriosclerosis, cerebral infarction, inflammation or restenosis after PTCA platelet aggregation in a patient in need thereof, said method comprising:

administering an effective amount of the pharmaceutical composition of claim 4 or 5 to said patient.

10. A method of treating circulatory disease, treating or suppressing platelet aggregation, circulatory disease, obstructive arteriosclerosis, cerebral infarction, inflammation or restenosis after PTCA platelet aggregation in a patient in need thereof, said method comprising:

administering an effective amount of the pharmaceutical composition of claim 6 or 7 to said patient.

* * * * *

UNITED STATES PATENT AND TRADEMARK OFFICE
CERTIFICATE OF CORRECTION

PATENT NO. : 6,949,553 B2
DATED : September 27, 2005
INVENTOR(S) : Tadakazu Tamai et al.

It is certified that error appears in the above-identified patent and that said Letters Patent is hereby corrected as shown below:

<u>Title page,</u>
Item [54], Title, should read -- ALIPHATIC COMPOUNDS, THEIR SYNTHESIS METHOD, AND UTILIZATION METHOD OF THE SAME --.

Signed and Sealed this

Twenty-third Day of May, 2006

JON W. DUDAS
*Director of the United States Patent and Trademark Office*